US007288768B2

(12) United States Patent
Gore et al.

(10) Patent No.: US 7,288,768 B2
(45) Date of Patent: Oct. 30, 2007

(54) METHOD FOR MEASURING THE AMOUNT OF AN ORGANIC SUBSTANCE IN A FOOD PRODUCT WITH INFRARED ELECTROMAGNETIC RADIATION

(75) Inventors: Jay P. Gore, West Lafayette, IN (US); Rakesh Singh, Bogart, GA (US); Abdullatif Tay, North Brunswick, NJ (US); Sivakumar Santhanakrishnan, Indianapolis, IN (US)

(73) Assignee: Purdue Research Foundation, West Lafayette, IN (US)

( * ) Notice: Subject to any disclaimer, the term of this patent is extended or adjusted under 35 U.S.C. 154(b) by 372 days.

(21) Appl. No.: 10/616,564

(22) Filed: Jul. 10, 2003

(65) Prior Publication Data

US 2004/0036022 A1 Feb. 26, 2004

Related U.S. Application Data

(60) Provisional application No. 60/396,851, filed on Jul. 18, 2002.

(51) Int. Cl.
*G01N 21/35* (2006.01)
*G01J 5/02* (2006.01)

(52) U.S. Cl. ............ 250/339.12; 250/339.11; 250/341.6; 250/343

(58) Field of Classification Search ........... 250/339.12, 250/339.01, 339.05, 339.11, 339.13, 343, 250/341.6; 356/237.1
See application file for complete search history.

(56) References Cited

U.S. PATENT DOCUMENTS 4,427,889 A 1/1984 Müller
4,655,225 A 4/1987 Dähne et al.
4,915,827 A * 4/1990 Rosenthal .................. 209/577
5,218,529 A * 6/1993 Meyer et al. ................ 702/28
5,239,180 A * 8/1993 Clarke .................. 250/339.11
5,321,265 A 6/1994 Block
5,448,069 A * 9/1995 Tobler et al. .......... 250/339.01
5,478,748 A * 12/1995 Akins et al. .................. 436/86
5,515,847 A 5/1996 Braig et al.
5,529,755 A 6/1996 Higashio et al.
5,533,509 A 7/1996 Koashi et al.
5,710,630 A 1/1998 Essenpreis et al.
5,743,262 A 4/1998 Lepper, Jr. et al.
5,755,672 A * 5/1998 Arai et al. .................. 600/547
5,900,634 A * 5/1999 Soloman ................ 250/339.11
6,005,076 A * 12/1999 Murray ....................... 530/377

(Continued)

FOREIGN PATENT DOCUMENTS

WO WO 03/016882 A1 2/2003

OTHER PUBLICATIONS

S. R. Ash et al., "Subcutaneous Ultrafiltration Fibers for Chemical Sampling of Blood: The Capillary Filtrate Collector (CFC)", *American Filtration Society*, 1993, pp. 316-319.

(Continued)

*Primary Examiner*—David Porta
*Assistant Examiner*—Faye Boosalis
(74) *Attorney, Agent, or Firm*—Barnes & Thornburg LLP

(57) ABSTRACT

A method for measuring the amount of an organic substance in a food product with infrared electromagnetic radiation.

25 Claims, 15 Drawing Sheets

14 10 28 12 26 16 18 22 26 30 20 24

U.S. PATENT DOCUMENTS

| | | | | |
|---|---|---|---|---|
| 6,025,597 | A | 2/2000 | Sterling et al. | |
| 6,049,727 | A | 4/2000 | Crothall | |
| 6,100,526 | A * | 8/2000 | Mayes | 250/339.11 |
| 6,113,541 | A | 9/2000 | Dias et al. | |
| 6,152,889 | A | 11/2000 | Sopp et al. | |
| 6,157,041 | A | 12/2000 | Thomas et al. | |
| 6,208,470 | B1 * | 3/2001 | Anderson et al. | 359/649 |
| 6,236,048 | B1 * | 5/2001 | Ditmarsen et al. | 250/339.12 |
| 6,316,772 | B1 * | 11/2001 | Egelberg | 250/339.11 |
| 6,483,583 | B1 * | 11/2002 | Wright et al. | 356/326 |
| 6,587,575 | B1 * | 7/2003 | Windham et al. | 382/110 |
| 6,646,264 | B1 * | 11/2003 | Modiano et al. | 250/339.07 |

OTHER PUBLICATIONS

E. M. Janle et al., "Determination of Glucose in Microliter Samples of In Vivo Ultrafiltrates and Microdialysates Using Amperometric Flow Injection Analysis with an Enzyme Reactor", *Current Separations*, 1993, vol. 12, No. 1, pp. 14-17.

D. A. Krohn, *Fiber Optic Sensors: Fundamentals and Applications*, 1992, pp. 21-23.

S. Santhanakrishnan et al., "On the Quantitative Measurement of Glucose in Biological Fluids", *Mid-IR Technical Report* #01-003, 2001, 18 pgs.

S. S. Krishnan et al., "Optimum Pathlength for Aqueous Solutions Transmission Measurements", *Mid-IR Technical Report* 190 01-002, 2000, 5 pgs.

G. L. Coté, "Noninvasive Optical Glucose Sensing—An Overview", *Journal of Clinical Engineering*, 1997, pp. 253-259.

Y. Gotshal et al., "Blood diagnostics using fiberoptic evanescent wave spectroscopy and neural networks analysis", *Sensors and Actuators B*, 1997, vol. 42, pp. 157-161.

K. Kajiwara et al., "Spectroscopic quantitative analysis of blood glucose by Fourier transform infrared spectroscopy with an attenuated total reflection prism", *Medical Process through Technology*, 1992, vol. 18, pp. 181-189.

Y. Mendelson et al., "Blood Glucose Measurement by Multiple Attenuated Total Reflection and Infrared Absorption Spectroscopy", *IEEE Transactions on Biomedical Engineering*, 1990, vol. 37, pp. 458-465.

S. R. Ash, "Subcutaneous Capillary Filtrate Collector for Measurement of Blood Glucose", *ASAIO*, 1992, pp. 416-420.

P. Geladi et al., "Partial Least-Squares Regression: A Tutorial", *Analytica Chemica Acta*, 1986, pp. 1-17.

S. A. Jimeno, "The Spanish toxic symptoms", *Trends in Analytical Chemistry*, 1982, vol. 1, pp. 4-6.

V. M. Kapoulas et al., "Detection of Virgin Olive Oil Adulteration with Refined Oils by Second-Derivative Spectrophotometry", *Food Chemistry*, 1987, vol. 23, pp. 183-192.

V. M. Kapoulas et al., "Detection of Adulteration of Olive Oil with Seed Oils by a Combination of Column and Gas Liquid Chromatography", *Journal of the American Oil Chemists' Society*, 1981, vol. 58, pp. 694-697.

A. Lanzou et al., "Detection of refined olive oil in virgin olive", *Grasas Aceites*, 1989, vol. 40, No. 6, pp. 385-388.

D. Marini et al., "Spectrophotofluorometric analysis of olive oil", *Revista Italiana Sostanze Grasse*, 1990, vol. 67, No. 2, pp. 95-99.

T. Mavromoustakos et al., "C-NMR Analysis of the Triacyglycerol Composition of Greek Virgin Olive Oils", *Magnetic Resonance in Chemistry*, 1997, vol. 35, pp. 3-7.

M. T. Morales et al., "Tentative analysis of virgin olive oil aroma by supercritical fluid extraction-high-resolution gas chromatrography-mass spectrometry", *Journal of Chromatography A*, 1998, vol. 819, pp. 267-275.

G. Morchio et al., "Detection of refined oils in virgin olive oil", *Rivista Italiana Sostanze Grasse*, 1989, vol. 66, No. 5, pp. 251-257.

S. A. Passaloglou-Emmanouillidou, "A comparative study of UV spectrophotometric methods for detection of olive oil adulteration by refined oils", *Zeitschrift tzir Lebensmittel-Untersuchung und-Forschung*, vol. 191, No. 2, pp. 132-134.

P. Sachhi et al., "Application of Carbon-13 NMR to the determination of mono- and diglycerides and free fatty acids in virgin and refined olive oil", *Rivista Italiana Sostanze Grasse*, 1990, vol. 67, No. 5, pp. 245-252.

R. Sacchi et al., "$^1$H and $^{13}$C-NMR of virgin olive oil. An Overview", *Magnetic Resonance in Chemistry*, 1997, vol. 35, pp. 133-145.

R. J. Sanchis et al., "Rapid HPLC procedure for the detection of adulteration of olive oil by seed oils", *Alimentaria* (*Madrid*), 1991, pp. 27-29.

L Küpper et al., "Authentication and Quantification of Extra Virgin Olive Oils by Attenuated Total Reflectance Infrared Spectroscopy Using SIlver Halide Fiber Probes and Partial Least-Squares Calibration", *Applied Spectroscopy*, 2001, No. 5, pp. 563-570.

M. Karlowatz et al., "Chemically Tapered Silver Halide Fibers: An Approach for Increasing the Sensitivity of Mid-Infrared Evanescent Wave Sensors", *Applied Spectroscopy*, 2000, No. 11, pp. 1629-1633.

L. Han et al., "NIR Fiber-Optic Method with Multivariate Calibration Analysis for Determination of Inorganic Compounds in Aqueous Solutions", *Applied Spectroscopy*, 2000, vol. 54, No. 10, pp. 1447-1452.

B. Lendi et al., "Fourier Transform Infrared Detection in Miniaturized Total Analysis Systems for Sucrose Analysis", 1997, *Analytical Chemistry*, 1997, vol. 69, No. 15, pp. 2877-2881.

D. Lefier et al., "Determination of Fat, Protein, and Lactose in Raw Milk by Fourier Transform Infrared Spectroscopy and by Analysis with a Conventional Filter-Based Milk Analyzer", *Journal of AOAC International* , 1996, vol. 79, No. 3, pp. 711-717.

Boston Electronics Corporation,"*puls*IR-Evaluation Kit Driver Instruction Manual", date unknown, 4 pgs.

IntraTec GmbH, "Proelectric detectors", 1999, 5 pgs.

* cited by examiner

METHOD FOR MEASURING THE AMOUNT OF AN ORGANIC SUBSTANCE IN A FOOD PRODUCT WITH INFRARED ELECTROMAGNETIC RADIATION

This application claims priority under 35 U.S.C. §119(e) to U.S. Provisional Patent Application Ser. No. 60/396,851 entitled "METHOD FOR MEASURING THE AMOUNT OF AN ORGANIC SUBSTANCE IN A FOOD PRODUCT WITH INFRARED ELECTROMAGNETIC RADIATION" which was filed on Jul. 18 2002 by Jay P. Gore et al. which is expressly incorporated by reference herein.

TECHNICAL FIELD OF THE INVENTION

The present invention generally relates to a method of measuring an amount of an organic substance contained within a food product. The present invention particularly relates to a method of measuring the amount of an organic substance contained within a food product utilizing a limited number of selected infrared wavelength bands.

BACKGROUND OF THE INVENTION

Adulteration of food products, involving the replacement of high cost ingredients with lower grade and cheaper substitutes can be very attractive and lucrative for a food manufacturer or raw material supplier. The adulteration of food products is not only a major economic fraud, but can also have major health implications to consumers. In the 1980s, more than 400 deaths and 20,000 casualties occurred from the disease known as "Spanish toxic syndrome," caused by the consumption of adulterated oil. Therefore, the detection of adulteration is of importance.

Olive oil production is a big business subject to serious attempts at fraudulent marketing of low-quality or adulterated oils. There are various methods for extracting the oil that yield different quality grades. Extra virgin olive oil is obtained from the olive *Olea europaca sativa* H by purely mechanical means, and the lower grade oils are obtained by solvent extraction, heat treatment, esterification, or refining. The composition of the oils is based on the fatty acids present in the tri-acyiglycerols and their location on the glycerol backbone. This composition varies not only with the type of oil and extraction method but also with geographical origin and meteorological effects during the growth and harvest of the olives. This variation can be used for oil authentication and the identification of adulteration. Various physical and chemical tests have been used to establish the authenticity of olive oil and to detect the level of adulterants in it. UV spectroscopy based on 208-210 and 310-320 nm has been widely used to detect the adulteration of virgin with the refined olive oil. A second derivative spectrometry method was reported to be able to detect the adulteration at a level of 6%.

Analysis of fatty acid profile after methylation using gas chromatography (GC) has been reported for the quantification of seed oils in olive oil. HPLC analysis of the fatty acid and triglycerides composition was also studied for detection of adulteration of olive oil. Nuclear magnetic resonance (NMR) analysis and a spectroflourometric methods have also been reported for detecting the adulteration of olive oil.

However, a drawback to some of these conventional methods of analyzing oils is that they are destructive and time-consuming, involving the hydrolysis and methylation of the resulting fatty acids. In addition, some of these approaches loose any information associated with the location of the fatty acids on the original glycerol backbone. Accordingly, authentication of the constituents of a food product is a major challenge in food product analysis.

Therefore, in light of the above discussion, it is apparent that what is needed is a method of measuring an amount of an organic substance contained within a food product that addresses one of more of the above discussed drawbacks.

SUMMARY OF THE DISCLOSURE

In one illustrative embodiment, there is provided a method of measuring an amount of an organic substance contained within a food product. The organic substance has an infrared absorption spectrum which includes a set (n) of wavelength regions. Each of the wavelength regions substantially correspond to an absorption band of the absorption spectrum. The method includes (a) detecting the intensity of a number of selected wavelength bands of infrared electromagnetic radiation influenced by the organic substance contained within the food product with a detection system, wherein (i) each of the selected wavelength bands substantially corresponds to one of the wavelength regions and (ii) the number of the selected wavelength bands is equal to n−1 or less, (b) generating an electrical signal in response to detecting the intensity of the number of the selected wavelength bands, (c) receiving the electrical signal with a signal processor configured to process the electrical signal with a quantification algorithm, and (d) processing the electrical signal with the quantification algorithm so as to provide a measurement of the amount of the organic substance contained within the food product.

In another illustrative embodiment, there is provided a method of measuring an amount of a vegetable seed oil contained within a food product. The vegetable seed oil has an infrared absorption spectrum which includes a set (n) of infrared wavelength regions. Each of the infrared wavelength regions substantially correspond to an infrared absorption band of the infrared absorption spectrum. The method includes (a) detecting the transmittance of a number of selected wavelength bands of infrared electromagnetic radiation absorbed by the vegetable seed oil contained within the food product with a detection system, wherein (i) each of the selected wavelength bands substantially corresponds to one of the wavelength regions and (ii) the number of the selected wavelength bands is equal to n−1 or less, (b) generating an electrical signal in response to detecting the transmittance of the infrared electromagnetic radiation, (c) receiving the electrical signal with a signal processor configured to process the electrical signal with a quantification algorithm, and (d) processing the electrical signal with the quantification algorithm so as to provide a measurement of the amount of the vegetable seed oil contained within the food product.

In yet another illustrative embodiment, there is provided a method of measuring an amount of milk fat in a food product. The milk fat has an infrared absorption spectrum which includes a set (n) of infrared wavelength regions. Each of the infrared wavelength regions substantially correspond to an infrared absorption band of the infrared absorption spectrum. The method includes (a) detecting the transmittance of a number of selected wavelength bands of infrared electromagnetic radiation absorbed by the milk fat contained within the food product with a detection system, wherein (i) each of the selected wavelength bands substantially corresponds to one of the wavelength regions and (ii) the number of the selected wavelength bands is equal to n−1 or less, (b) generating an electrical signal in response to detecting the transmittance of the infrared electromagnetic radiation, (c) receiving the electrical signal with a signal processor configured to process the electrical signal with a quantification algorithm, and (d) processing the electrical signal with the quantification algorithm so as to provide a measurement of the amount of the milk fat contained within the food product.

In still another illustrative embodiment, there is provided a method of measuring a concentration of an organic substance contained within a food product. The organic substance has an infrared absorption spectrum which includes a set (n) of infrared wavelength regions. Each of the infrared wavelength regions substantially correspond to an infrared absorption band of the infrared absorption spectrum. The method includes (a) detecting the transmittance of a number of selected wavelength bands of infrared electromagnetic radiation absorbed by the organic substance contained within the food product with a detection system, wherein (i) each of the selected wavelength bands substantially corresponds to one of the wavelength regions and (ii) the number of the selected wavelength bands is equal to n−1 or less, (b) generating an electrical signal in response to detecting the transmittance of the selected infrared electromagnetic radiation wavelength bands, (c) receiving the electrical signal with a signal processor configured to process the electrical signal with a mathematical model, and (d) processing the electrical signal with the mathematical model so as to provide a measurement of the concentration of the organic substance contained within the food product.

In yet another illustrative embodiment, there is provided a method of measuring an amount of an organic substance contained within a food product. The organic substance has an infrared absorption spectrum which includes a set (n) of wavelength regions. Each of the wavelength regions substantially correspond to an absorption band of the absorption spectrum. The method includes (a) illuminating the food product with infrared electromagnetic radiation, wherein the infrared electromagnetic radiation includes one or more wavelength bands of the infrared electromagnetic radiation which are absorbed by the organic substance contained within the food product, (b) selecting a number of the wavelength bands of the infrared electromagnetic radiation, wherein (i) each of the selected wavelength bands substantially corresponds to one of the wavelength regions and (ii) the number of the selected wavelength bands is a subset of (n), (c) detecting the intensity of only (i) the subset of the selected wavelength bands absorbed by the organic substance contained within the food product with a detection system and (ii) the number of reference wavelength bands, (d) generating one or more electrical signals in response to detecting the intensity of only the subset of the selected wavelength bands, (e) receiving the one or more electrical signals with a signal processor configured to process the electrical signals with a quantification algorithm, and (f) processing the one or more electrical signals with the quantification algorithm so as to provide a measurement of the amount of the organic substance contained within the food product.

In still another illustrative embodiment, there is provided a method of measuring an amount of an organic substance contained within a food product. The organic substance has an infrared absorption spectrum which includes a set (n) of wavelength regions. Each of the wavelength regions substantially correspond to an absorption band of the absorption spectrum. The method includes (a) illuminating the food product with infrared electromagnetic radiation, (b) detecting the intensity of the infrared electromagnetic radiation that is absorbed by the organic substance contained within the food product, wherein (i) the intensity detection is restricted to a number of selected wavelength bands of infrared electromagnetic radiation, (ii) each of the selected wavelength bands substantially corresponds to one of the wavelength regions, and (iii) the number of the selected wavelength bands is a subset of (n), (c) generating an electrical signal in response to detecting the intensity of the subset of the selected wavelength bands, (d) receiving the electrical signal with a signal processor configured to process the electrical signal with a quantification algorithm, and (e) processing the electrical signal with the quantification algorithm so as to provide a measurement of the amount of the organic substance contained within the food product.

In yet another illustrative embodiment, there is provided a method of measuring an amount of an organic substance contained within a food product. The organic substance has an infrared absorption spectrum which includes a set (n) of wavelength regions. Each of the wavelength regions substantially correspond to an absorption band of the absorption spectrum. The method includes (a) illuminating the food product with infrared electromagnetic radiation, wherein the infrared electromagnetic radiation includes one or more wavelength bands of the infrared electromagnetic radiation which are absorbed by the organic substance contained within the food product, (b) selecting a number the wavelength bands of the infrared electromagnetic radiation, wherein (i) each of the selected wavelength bands substantially corresponds to one of the wavelength regions and (ii) the number of the selected wavelength bands is a subset of (n), (c) detecting with a detection system the intensity of the infrared electromagnetic radiation, and (d) processing with a mathematical model spectral data only from the subset of the selected wavelength bands absorbed by the organic substance contained within the food product.

It is therefore an object of the present invention to provide a new and useful method of measuring an amount of an organic substance contained within a food product.

It is another object of the present invention to provide an improved method of measuring an amount of an organic substance contained within a food product.

The above and other objects, features, and advantages of the present invention will become apparent from the following description and attached drawings.

DETAILED DESCRIPTION OF THE PREFERRED EMBODIMENT

Figure 1:
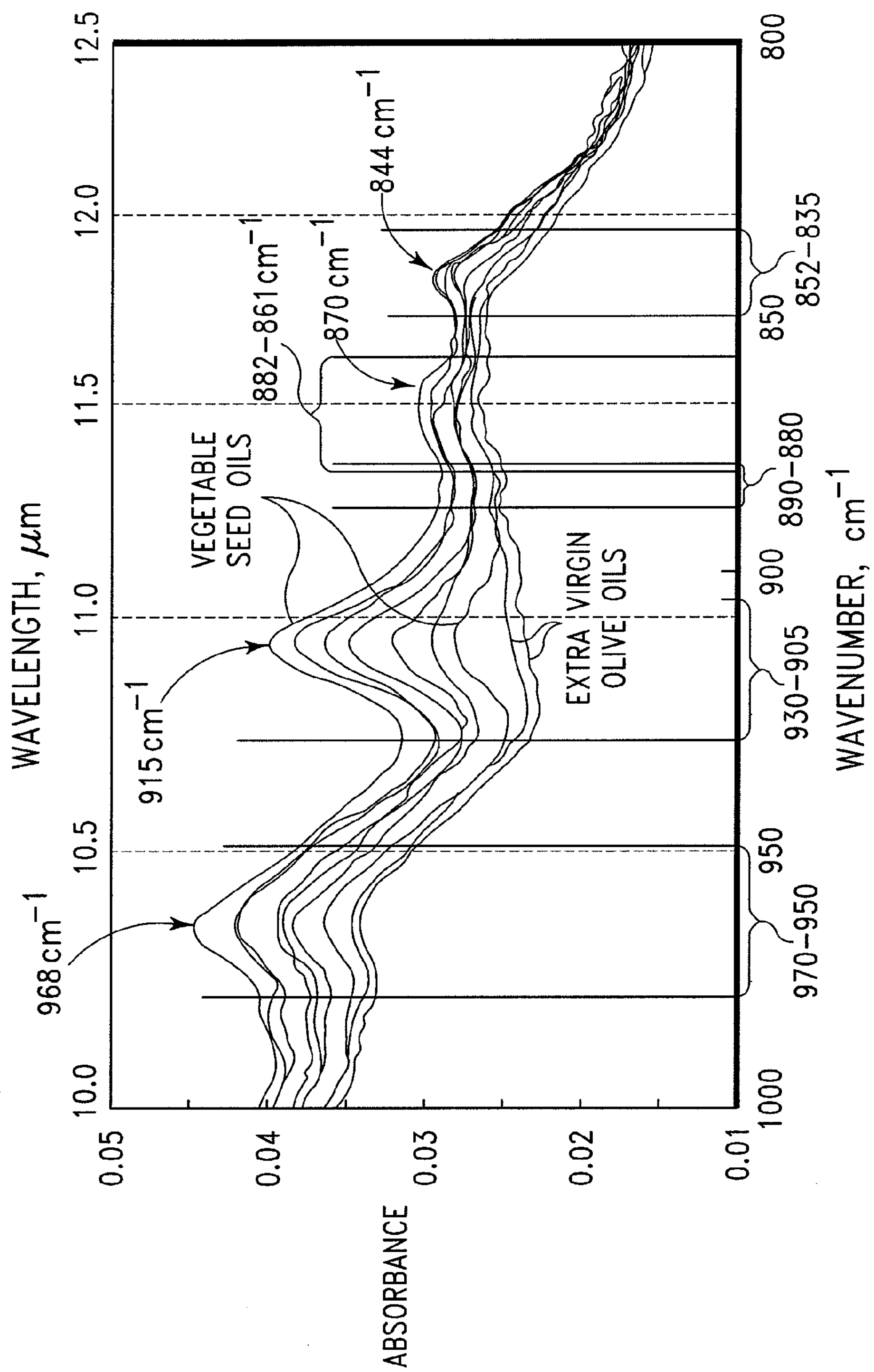
FIG. 1 is an ATR spectra of extra virgin olive oil and a number of vegetable seed oils.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Organic substances can influence electromagnetic radiation. For example, when electromagnetic radiation encounters an organic substance the radiation can be absorbed or transmitted, depending upon the nature of the organic molecules it encounters. If the electromagnetic radiation is absorbed, then the absorption gives rise to absorption bands at particular wavelength regions of an absorption spectrum of the organic substance. (Note that examples of ways to express wavelength regions include, but are not limited to, frequency, wavelength, or wavenumber.)

With respect to infrared electromagnetic radiation (e.g. coherent and incoherent electromagnetic radiation), it should be understood that, as discussed in greater detail below, an organic substance has an infrared absorption spectrum which includes a set (n) of wavelength regions with each wavelength region corresponding to an absorption band of the absorption spectrum. For example, FIG. 1 shows the infrared absorption spectrum of several organic substances of interest. In particular, FIG. 1 shows the infrared absorption spectrum of several food products. Note that a food product as used herein, includes, but is not limited to, substances consumed for their nutritive value. Also note that a food product as used herein also includes substances consumed primarily for recreational purposes, such as alcoholic beverages, for example wine. Further note that, while examples of the methods described herein utilize incoherent infrared electromagnetic radiation, coherent infrared electromagnetic radiation can also be utilized.

Now referring to FIG. 1 there is shown the infrared absorption spectrum of several vegetable seed oils (e.g. canola, corn, peanut, sesame, soybean, sunflower, and walnut oil) in comparison with extra virgin olive oil in the 1000-800 $cm^{-1}$ wavenumber range. As shown in FIG. 1, the infrared absorption spectrum of vegetable seed oils show absorption bands centered at about 844 $cm^{-1}$, about 870 $cm^{-1}$, about 915 $cm^{-1}$, and about 968 $cm^{-1}$. Accordingly, these vegetable seed oils have a set (n) of absorption bands within the 800-1000 $cm^{-1}$ range of the spectrum. In this case (n) equals 4, i.e. an absorption band centered at about 844 $cm^{-1}$, about 870 $cm^{-1}$, about 915 $cm^{-1}$, and about 968 $cm^{-1}$. It should be appreciated that, as shown in FIG. 1, at least a portion of each absorption band occurs between two selected wavenumbers. For example, the absorption band centered at about 915 $cm^{-1}$ occurs between wavenumbers about 905 $cm^{-1}$ and about 930 $cm^{-1}$. It should be understood that the area of the spectrum between two wavenumbers, at which an absorption band occurs, is referred to herein as a wavelength region. As such, each absorption band has a substantially corresponding selected wavelength region. For example, the absorption band at about 844 $cm^{-1}$ has a substantially corresponding wavelength region of about 835 $cm^{-1}$ to about 852 $cm^{-1}$. In a similar manner, the absorption band at about 870 $cm^{-1}$ has a substantially corresponding wavelength region of about 861 $cm^{-1}$ to about 882 $cm^{-1}$. The absorption band at about 968 $cm^{-1}$ has a substantially corresponding wavelength region of about 950 $cm^{-1}$ to about 970 $cm^{-1}$. Therefore, it should be appreciated that each absorption spectrum also has a set (n) of wavelength regions, and since each absorption band has a substantially corresponding wavelength region, the set (n) of wavelength regions equals the set (n) of absorption bands. For example, with respect to the absorption spectrum of the vegetable seed oils shown in FIG. 1, the set (n) of absorption bands equals 4 and accordingly the set (n) of wavelength regions also equals 4.

As discussed above, the vegetable seed oils absorption spectrum of FIG. 1 has 4 absorption bands respectively centered at about 844 $cm^{-1}$, about 870 $cm^{-1}$, about 915 $cm^{-1}$, and about 968 $cm^{-1}$. It should be appreciated that these vegetable seed oils not only absorbs infrared electromagnetic radiation at each particular wavenumber mentioned above, but also at higher and lower wavenumbers around each of the aforementioned centered wavenumbers. In other words, an absorption band of a vegetable seed oil has a width, and therefore will absorb a range or a wavelength band of infrared electromagnetic radiation. As discussed above, a wavelength region is the area of the spectrum between two wavenumbers at which an absorption band occurs. Accordingly, a wavelength band is the range of wavenumbers (or other methods of measuring electromagnetic radiation including, but not limited to, frequency or wavelengths) within a wavelength region at which an organic substance absorbs electromagnetic radiation. In other words, each wavelength band substantially corresponds to a wavelength region. For example, as previously mentioned, the absorption spectrum of each vegetable seed oil shown in FIG. 1, has 4 wavelength regions, i.e. (i) about 835 $cm^{-1}$ to about 852 $cm^{-1}$, (ii) about 861 $cm^{-1}$ to about 882 $cm^{-1}$, (iii) about 905 $cm^{-1}$ to about 930 $cm^{-1}$, and (iv) about 950 $cm^{-1}$ to about 970 $cm^{-1}$. Therefore, the absorption spectrum of each vegetable seed oil shown in FIG. 1 also has 4 substantially corresponding wavelength bands at which the vegetable seed oil absorbs the electromagnetic radiation, i.e. (i) about 835 $cm^{-1}$ to about 852 $cm^{-1}$, (ii) about 861 $cm^{-1}$ to about 882 $cm^{-1}$, (iii) about 905 $cm^{-1}$ to about 930 $cm^{-1}$, and (iv) about 950 $cm^{-1}$ to about 970 $cm^{-1}$.

However, note that a wavelength region and a wavelength band do not necessarily have to be a range if the organic substance of interest and the nature of the electromagnetic radiation is such that a single wavenumber (frequency or wavelength) can be utilized in the methods described herein. Therefore, as used herein, the terms "wavelength region" and "wavelength band" can be a range, or can consist of a single wavenumber (frequency or wavelength).

Still referring to FIG. 1, it should be understood that the absorption spectrum shown therein has a reference wavelength band as well.

A reference wavelength band is similar to one of the above described wavelength bands, however in contrast to a wavelength band, a reference wavelength band is a range of wavenumbers at which (i) the organic substance of interest (e.g. the adulterating substance) does not substantially influence the electromagnetic radiation but other compounds present within the food product do influence the electromagnetic radiation or (ii) no organic substance present within the food product substantially influences the electromagnetic radiation. For example, a range of wavenumbers at which the organic substance of interest does not substantially absorb infrared electromagnetic radiation, while other organic substances present in the food product do absorb infrared electromagnetic radiation, can be utilized as a reference wavelength band in the methods described herein. In addition, a range of wavenumbers at which no organic substance present in the food product substantially absorbs infrared electromagnetic radiation can be utilized as a reference wavelength band in the methods described herein. In particular, the organic substance of interest with respect to the absorption spectrum shown in FIG. 1 is vegetable seed oil, accordingly potential wavenumber ranges which can serve as reference wavelength bands are (i) those wavenumber ranges at which vegetable seed oil substantially does not absorb the infrared electromagnetic radiation while other compounds present in the sample do absorb the infrared electromagnetic radiation and (ii) those wavenumber ranges at which no organic substance substantially absorbs the infrared electromagnetic radiation. Preferably, a reference wavelength band is selected where no organic substance substantially influences or absorbs the electromagnetic radiation, however this is not necessary for the performance of the methods described herein.

In particular, as stated above, the organic substance(s) of interest with respect to the absorption spectrum shown in FIG. 1 is vegetable seed oil, accordingly a potential wavenumber range which can serve as a reference wavelength band are (i) those wavenumber ranges at which a vegetable seed oil substantially does not absorb the infrared electromagnetic radiation as compared to a wavelength band while other compounds present in the sample may or may not absorb the infrared electromagnetic radiation and (ii) those wavenumber ranges at which no organic substance present in the food product substantially absorbs the infrared electromagnetic radiation. Selecting a reference wavelength band having the above described characteristics allows the spectral data (e.g. absorbance) obtained from detecting electromagnetic radiation within a particular reference wavelength band to be utilized as a baseline measurement. This baseline measurement data is also processed with the aforementioned mathematical model to obtain a measurement of the amount of the organic substance of interest present within the food product. One specific example of a reference wavelength band is shown in FIG. 1, i.e. one at about 890 $cm^{-1}$ to about 880 $cm^{-1}$.

To provide a measurement of the amount of an organic substance contained within a food product, the food product is illuminated with electromagnetic radiation, such as infrared electromagnetic radiation. For example, a beam of incoherent infrared electromagnetic radiation can be passed through a food product, such as extra virgin olive oil, so that the organic substance of interest contained within the food product influences the electromagnetic radiation. Preferably, the organic substance contained within the food product absorbs the electromagnetic radiation so as to create an absorption spectrum which, as discussed above, includes a set (n) of wavelength regions where each of the wavelength regions substantially correspond to an absorption band of the absorption spectrum. After illuminating the food product with the electromagnetic radiation, the intensity (e.g. detecting the transmittance) of the wavelength bands and reference wavelength bands are detected with a detection system. In particular, it should be understood that preferably the intensity of only the selected wavelength band(s) and the reference band(s) are detected with the detection system. In the alternative, the intensity of other wavelength(s) of electromagnetic radiation in addition to the selected wavelength band(s) and the reference band(s) can be detected, but only the data from the selected wavelength band(s) and the reference bands is utilized to measure the amount of the organic substance of interest contained within the food product. Furthermore, as previously mentioned, it should be understood that not all of the wavelength bands and reference wavelength bands are detected. In particular, only the select number of wavelength bands of the absorption spectrum are detected along with only the select number of reference wavelength bands. Therefore, it should be appreciated that preferably only the selected wavelength bands and reference wavelength bands are detected with the detection system while the rest of the electromagnetic radiation is substantially prevented from being detected by the detection system. For example, the electromagnetic radiation not included in the selected wavelength bands and reference wavelength bands can be substantially filtered out prior to reaching the detection system. In other words, the detection of the wavelength bands and reference wavelength bands is restricted to a select number of wavelength bands of electromagnetic radiation and a select number of reference wavelength bands of electromagnetic radiation. In particular, the number of selected wavelength bands of electromagnetic radiation is equal to $n-1$ or less. That is, the number of selected wavelength bands of electromagnetic radiation is a subset of (n).

With respect to which particular wavelength band, or combination of wavelength bands, is/are selected for detection is dependent upon which wavelength band(s), in combination with the selected reference wavelength band(s), yields spectral data for processing with a mathematical model so as to provide a useful measurement of the amount of organic substance contained within the food product. What is meant herein by "useful" measurement is that the measurement of the amount of organic substance contained with the food product is accurate and/or precise enough such that it would be acceptable to utilize in a particular measurement, assay, or application. For example, if a method described herein is utilized in providing a measurement of the amount of vegetable seed oil contained within extra virgin olive oil, the wavelength band(s) and reference wavelength band(s) must be selected so that the spectral data supplied to the mathematical model from the combination of these bands results in a vegetable seed oil measurement that is accurate and/or precise enough such that it informs the user of the extra virgin olive oil as to whether the olive oil has an acceptable amount of vegetable seed oil contained therein. For example, if the olive oil contains more than an acceptable amount of vegetable seed oil then the user of the olive oil can identify the olive oil as being adulterated with vegetable seed oil. What is an acceptable amount of an organic substance will be determined by the user of the food product.

Factors to consider when selecting which wavelength band(s) to detect include for example (i) ensuring that the absorption band contained within the wavelength band is, or includes, an absorption band of the organic substance of interest, (ii) selecting a wavelength band which has relatively strong absorption, and (iii) selecting a wavelength band where the strength of the wavelength band correlates well with the amount of organic substance of interest contained in the food product. In addition, it is preferable that the selected wavelength band(s) is relatively free of interference from absorption bands caused by substances other than the organic substance of interest present in the food product (e.g. the selected wavelength band is separated from the wavelength band of the potentially interfering substance). However, it should be understood that in order to utilize the methods described herein, the selected wavelength band(s) does not have to be free of interfering absorption bands caused by substances other than the organic substance of interest. Accordingly, a selected wavelength band(s) may be relatively free of interference from absorption bands caused by substances other than the organic substance of interest, or the selected wavelength band(s) may include interfering absorption bands caused by substances other than the organic substance of interest. Therefore, it should be appreciated that the selected wavelength band(s) can (i) be relatively free of interference from absorption bands caused by substances other than the organic substance of interest present in the food product, (ii) include interfering absorption bands caused by substances other than the organic substance of interest present in the food product, or (iii) be a combination of selected wavelength bands in which some are relatively free of interference from absorption bands caused by substances other than the organic substance of interest while others include interfering absorption bands caused by substances other than the organic substance of interest.

Furthermore, the particular mathematical model (e.g. algorithm) and wavelength band(s) and reference wavelength band(s) selected for a particular sensor configuration (discussed below) are determined by the performance of the calibration procedure (discussed below) used for a specific food product. Moreover, in order to obtain a useful measurement from a particular sensor configuration, the mathematical model, selected wavelength band(s), and selected reference wavelength band(s) may differ depending upon the nature of the food product the organic substance of interest is contained within. For example, different selected wavelength band(s) and selected reference wavelength band(s), in addition to a different mathematical model may be needed depending upon whether the organic substance is contained within for example, red wine or white wine. Additional factors to consider are measurement accuracy requirements and the economics of the electromagnetic radiation source, optical filters, and detection elements. It should be appreciated that each of the aforementioned factors for a particular application of the methods described herein can be determined by one of ordinary skill in the art by routine experimentation.

After identifying wavelength bands that meet one or more of the aforementioned criteria, which wavelength bands are actually selected for detection and utilization in one of the methods described herein is determined. In other words, different combinations of wavelength bands, or a single wavelength band, along with one or more reference wavelength bands are utilized until it is determined which combination yields a useful measurement.

The detection system generates an electrical signal as a result of detecting the intensity of the selected wavelength band(s) and reference wavelength band(s). The electrical signal is processed to yield data which is utilized to provide a useful measurement of the amount of the organic substance of interest contained within the food product. For example, data generated by the electrical signal can be processed by a mathematical model, such as a quantification algorithm, so as to provide a useful measurement of the amount of the organic substance of interest contained within the food product.

It should be appreciated that detecting and processing spectral data only from the selected wavelength band(s) and reference wavelength band(s) simplifies the process of providing a useful measurement of the amount of an organic substance of interest contained within a food product. For example, since an apparatus for performing a method described herein only detects and processes spectral data from a select number of wavelength bands and reference wavelength bands it is less complex as compared to an apparatus configured to detect and process spectral data from all of the wavelength bands of an absorption spectrum. Accordingly, an apparatus configured to perform one of the methods described herein lends itself to being smaller, compact, and portable.

While the above description is directed to the preferred method of limiting the detection to select wavelength bands and reference wavelength bands, an alternative embodiment of a method for measuring an amount of an organic substance contained within a food product is to detect all of the wavelength bands, but only process the spectral data from the aforementioned selected wavelength bands with the mathematical model.

Figure 2:
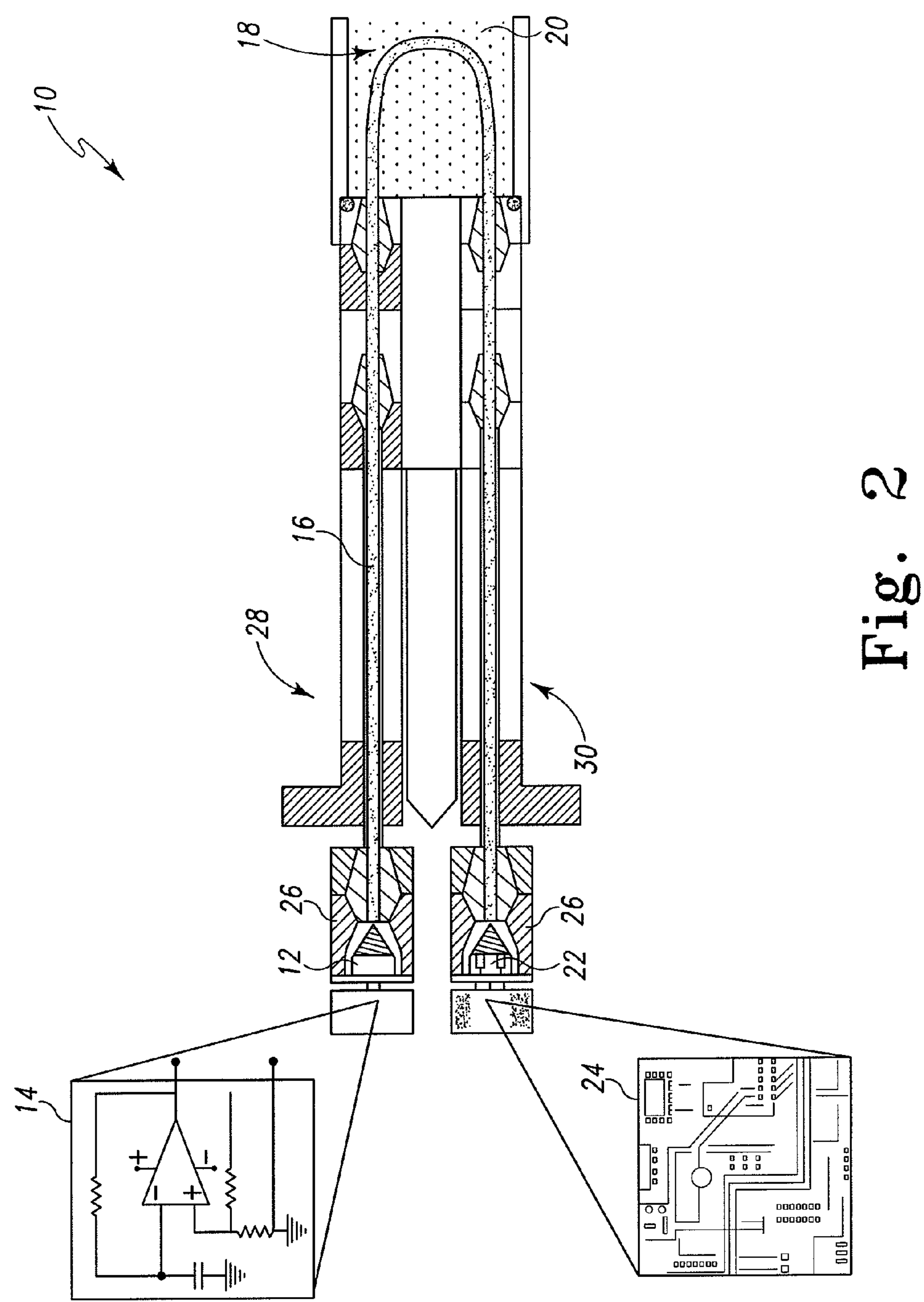
FIG. 2 is a schematic representation of a sensor.

Now referring to FIG. 2, there is shown an example of a fiber optic evanescent wave sensor 10 which can be utilized in the methods described herein. In particular, the spectral data obtained from this type of sensor 10 can be utilized in the quantification of an organic substance contained in a food product such as extra virgin olive oil or milk. A fiber optic evanescent wave sensor of the type shown in FIG. 2 is described by Kupper, L., Heise, H. M., Lampen, P., Davies, A. N. and McIntyre, P. in "Authentication and Quantification of Extra Virgin Oils by Attenuated Total Reflectance Infrared Spectroscopy Using Silver Halide Fiber Probes and Partial Least-Squares Calibration," Applied Spectroscopy, 55(5), pp. 563-570 (2001), which is incorporated herein by reference. Another fiber optic evanescent wave sensor of the type shown in FIG. 2 is described by Karlowatz, M., Kraft, M., Eitenberger, E., Mizaikoff, B. and Katzir, A. in "Chemically Tapered Silver Halide Fibers: An Approach for Increasing the Sensitivity of Mid-Infrared Evanescent Wave Sensors," *Applied Spectroscopy*, 54(11), pp. 1629-1633 (2000), which is incorporated herein by reference. Still another fiber optic evanescent wave sensor of the type shown in FIG. 2 is described by Han, L., Lucas, D., Littlejohn, D., and Kyauk, S. in "NIR Fiber-Optic Method with Multivariate Calibration Analysis for Determination of Inorganic Compounds in Aqueous Solutions," *Applied Spectroscopy*, 54(10), pp. 1447-1452 (2000), which is also incorporated herein by reference.

Briefly, sensor 10 shown in FIG. 1 includes a pulsed infrared source 12, a modulator and power supply circuit 14, a pair of optical couplers 26, and an optical fiber 16. Sensor 10 also includes a multichannel detector 22 and a signal conditioning, data acquisition and processing circuit 24.

Pulsed infrared source 12 is electrically coupled to circuit 14. Multichannel detector 22 is electrically coupled to processing circuit 24. Pulsed infrared source 12 and multichannel detector 22 are operatively coupled to optical fiber 16 via optical couplers 26. In particular, (i) a transmitting portion 28 of optical fiber 16 is operatively coupled to pulsed infrared source 12 and (ii) a receiving portion 30 of optical fiber 16 is operatively coupled to processing circuit 24. Note that optic fiber 16 is unclad through a portion of their length where food product 20 (e.g. olive oil) flows over the optic fiber 16. The length of this portion is determined by the signal-to-noise ratio requirements. The attenuation or absorbance of electromagnetic radiation advanced through optic fiber 16 due to the organic substances contained within food product 20 takes place via an evanescent wave phenomenon. Note that sensor 10 can include optical bandpass filters that limit the range of wavelengths of electromagnetic radiation which pass to detector 22 to those selected in the manner described above.

When operating sensor 10 a power supply provides power to source 12 such that source 12 generates a beam of incoherent infrared electromagnetic radiation directed toward transmitting portion 28 of optical fiber 16. The radiation is then transmitted through optic fiber 16 and thus passes through food product 20. Certain wavelengths of the radiation are absorbed by organic substances contained within food product 20 as the radiation passes therethrough. After passing through food product 20 the selected wavelength band and the selected reference wavelength band interacts with detector 22. Detector 22 generates an electrical signal(s) in response to interacting with a wavelength band or the reference wavelength band. The electrical signal is communicated to processing circuit 24. Processing circuit 24 then processes the electrical signal(s) with a mathematical model, such as a quantification algorithm, so as to provide a useful measurement of the amount of the organic substance of interest contained within food product 20.

Figure 3A:
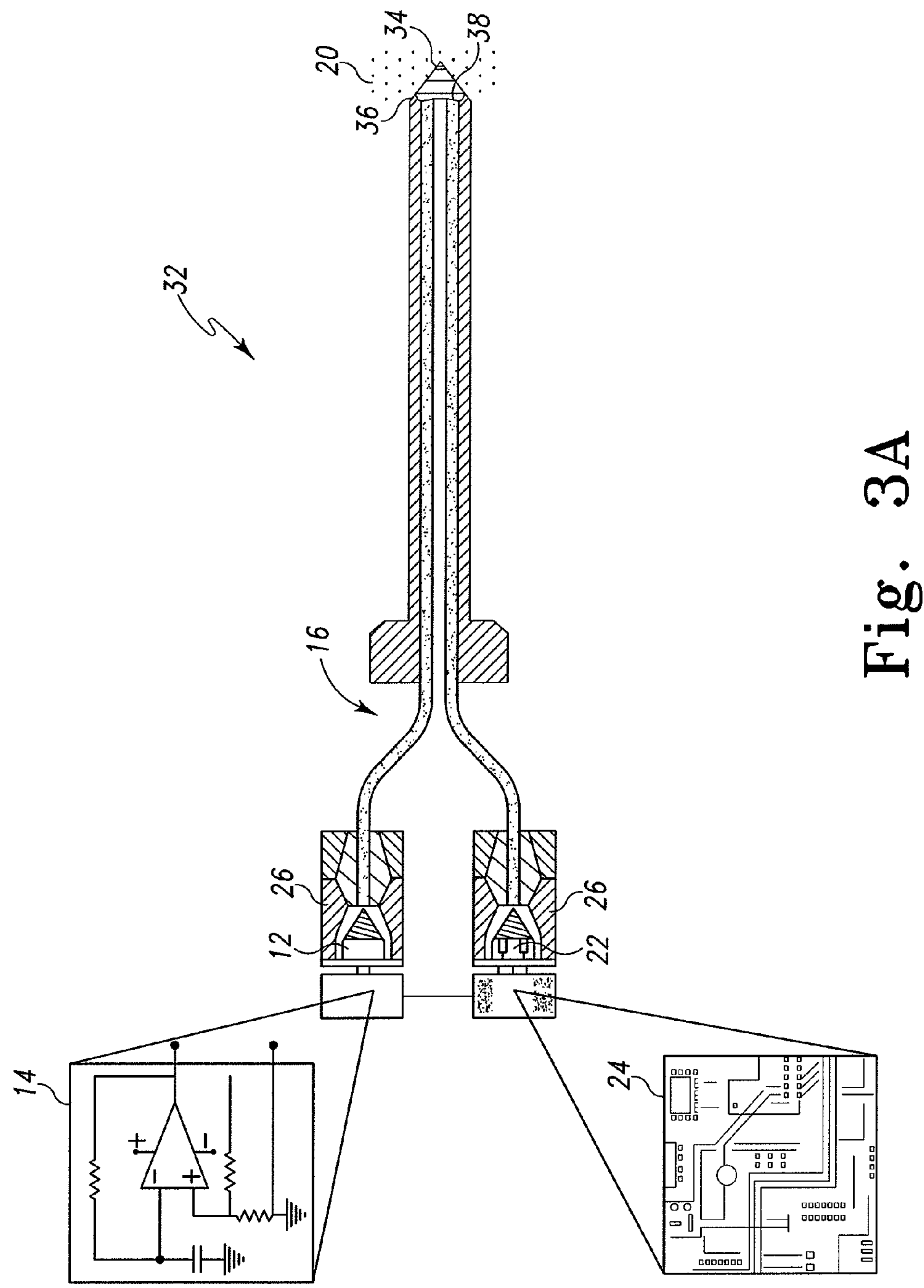
FIG. 3A is a schematic representation of a sensor.

Now referring to FIG. 3A, there is shown an example of an ATR fiber optic evanescent wave sensor 32 which can be utilized in the methods described herein. Sensor 32 is substantially similar to sensor 10 described above and thus the same reference numbers are used to indicate the corresponding components. In addition, since sensor 32 is similar to sensor 10 and operates in a similar manner, only substantial differences between sensor 32 and sensor 10 are briefly discussed herein.

As previously mentioned, the construction of sensor 32 is similar to sensor 10 except that a transmitting end 36 and a receiving end 38 of fiber 16 are separate units and they both terminate at an ATR crystal 34 operatively coupled thereto. Food product 20 is in contact with ATR crystal 34 but does not come in contact with optical fiber 16.

Sensor 32 is also based on the evanescent wave principle mentioned above. However, with sensor 32 the evanescent wave penetrates into food product 20 via ATR crystal 34 which is kept in contact food product 20. The electrical signals are generated and processed in a manner similar to that discussed above in reference to sensor 10.

Figure 3B:
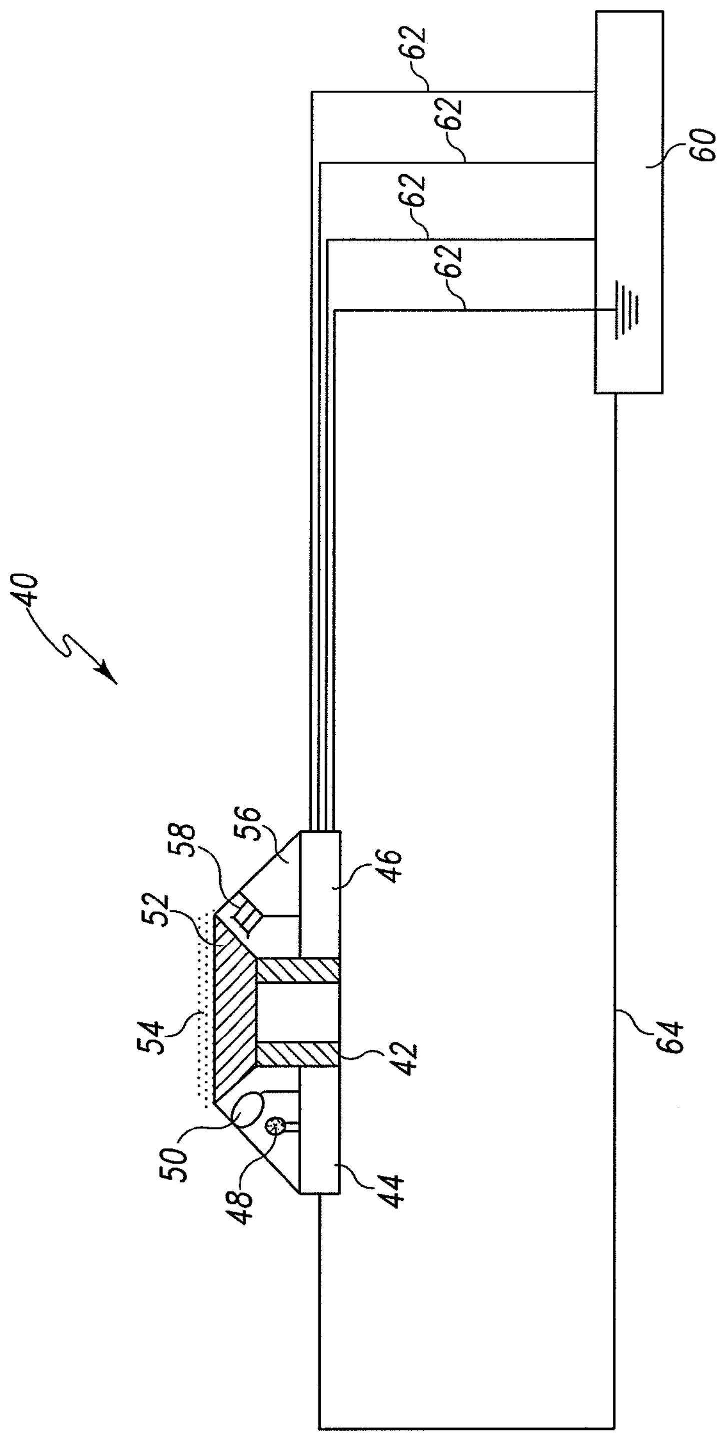
FIG. 3B is another schematic representation of a sensor.

Now referring to FIG. 3B there is shown an example of a miniature ATR sensor 40 which can be utilized in the methods described herein. Sensor 40 includes a base 42, a regulated power supply 44 operatively coupled to base 42 and a detector signal conditioning and amplification circuit 46 also operatively coupled to base 42. Sensor 40 further includes an infrared source 48 and focusing optics 100 operatively coupled to power supply 44. Infrared source 48 and focusing optics 100 are positioned relative to an ATR crystal 52 so that infrared electromagnetic radiation generated by infrared source 48 is directed through ATR crystal 52 and into a food product 54 by focusing optics 100. Sensor 40 also includes a detection element 56, such as a multichannel detector, operatively coupled to a filter assembly 58. Detection element 56 is positioned relative to ATR crystal 52 such that infrared electromagnetic radiation being emitted through ATR crystal 52 impinges onto filter assembly 58 and detection element 56. Sensor 40 further includes a mode-lock amplifier 60 which is operatively coupled to detector signal conditioning and amplification circuit 46 and power supply 44 via electrical lines 62 and electrical line 64, respectively.

When operating sensor 40 power supply 44 provides power to infrared source 48 such that infrared source 48 generates a beam of infrared electromagnetic radiation directed toward focusing optics 50. Focusing optics 50 directs the radiation through a food product 54 positioned in contact with ATR crystal 52. As discussed above, certain wavelengths of the radiation are absorbed by organic substances contained within food product 54 as the radiation passes therethrough. The radiation exits the ATR crystal 52 positioned in contact with food product 54 and interacts with filter assembly 58. Filter assembly 58 restricts the infrared electromagnetic radiation allowed to substantially pass therethrough to the selected wavelength bands and the selected reference wavelength band. Each selected wavelength band and one or more selected reference wavelength bands interact with a detection element 56 which generates an electrical signal in response to interacting with a wavelength band or the reference wavelength band. The electrical signal is communicated to mode-lock amplifier 60 via the aforementioned electrical lines. Each electrical signal is then communicated to a processor (such as an integrated circuit; not shown) via an electrical line (not shown). The processor then processes the electrical signals with a mathematical model, such as a quantification algorithm, so as to provide a useful measurement of the amount of the organic substance of interest contained within food product 54.

The following example illustrates utilizing one wavelength band and one reference wavelength band for providing a measurement of an adulterant in extra virgin olive oil.

Figure 4:
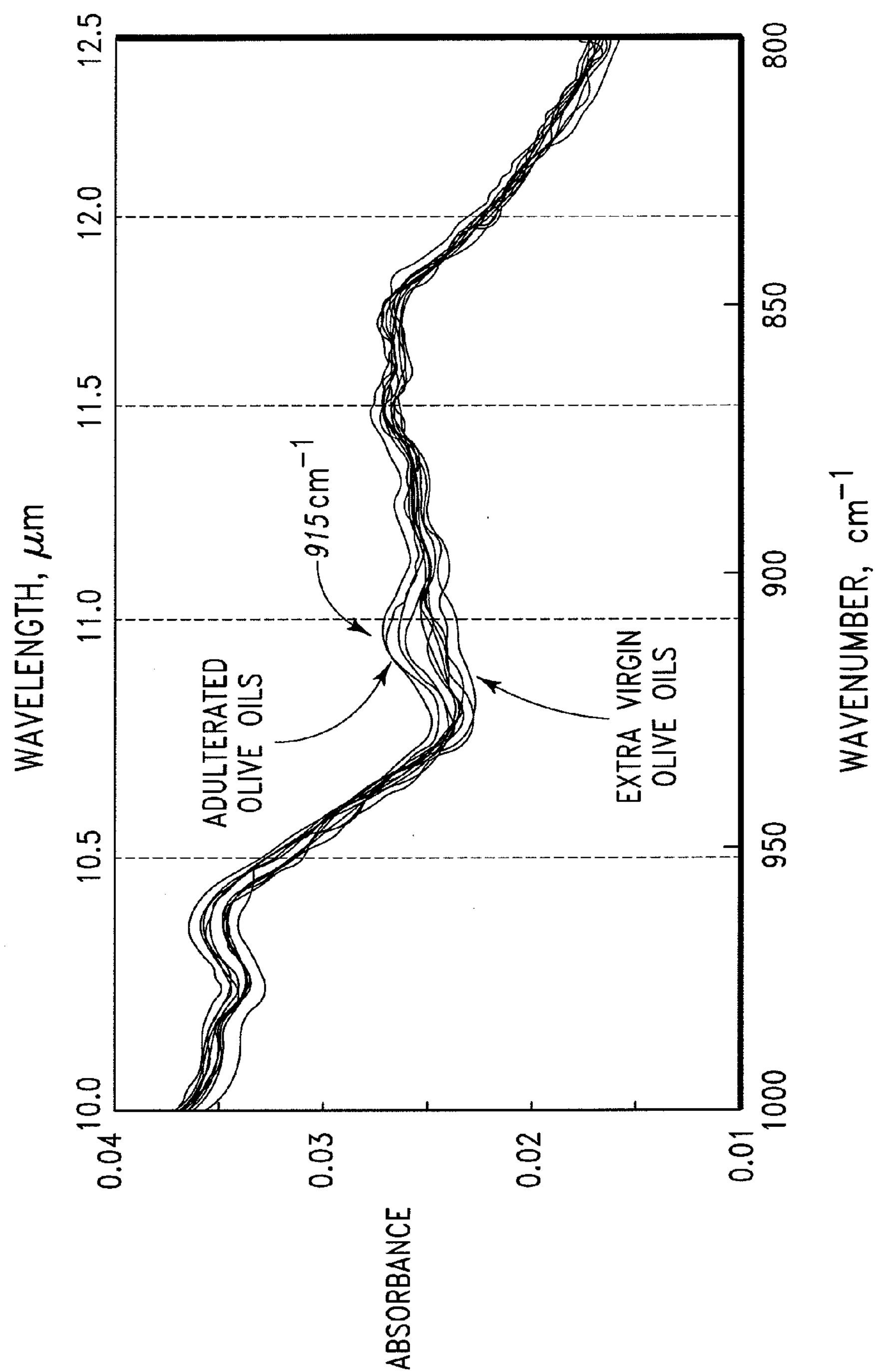
FIG. 4 is an ATR spectra of extra virgin olive oil adulterated with varying quantities of sunflower oil.

The absorption peaks due to the different components in the extra virgin and adulterated olive oils are seen in the 1000-800 $cm^{-1}$ (10.0-12.5 μm) range shown in FIG. 4. In this figure, the major absorption bands due to the C—O—C stretching and C—H bending are identifiable. These are due to the presence of fat in oils. Of these the absorption band centered at about 915 $cm^{-1}$ (10.9 μm) is present in the adulterant and absent in pure olive oil. Accordingly, the absorption band centered at about 915 $cm^{-1}$ was selected as the most suitable one for detecting the presence of the adulterant sunflower oil in olive oil. Furthermore, as discussed above, the absorption spectra of extra virgin olive oil was compared with those of other vegetable seed oils including: canola, corn, peanut, sesame, soybean, sunflower and walnut oils. As previously discussed, FIG. 1 shows the infrared absorption spectra of these oils in comparison to olive oils in the spectral range 1000-800 $cm^{-1}$. Based upon the spectra shown in FIG. 1 it should be appreciated that the detection of these oils in extra virgin olive oil is also possible utilizing the methods described herein.

To determine whether a sample of extra virgin oil is adulterated, the integrated absorbance occurring in one wavelength band and one reference wavelength band were calculated from the measured spectra of the solutions having the adulterant present at different concentrations. For example, the integrated absorbance occurring in one wavelength band and one reference wavelength band were calculated from the measured spectra of olive oil containing 0%, 2%, 5%, 8%, and 10% sunflower oil. The reference wavelength band is used as a reference band and is simply used to ratio out the baseline and reference signal variations. Further, the integrated absorbances are divided by the bandwidth to avoid scaling effects. From this data a ratio of the integrated absorbance occurring in about the 930-905 $cm^{-1}$ wavelength band and the integrated absorbance occurring in about the 890-880 $cm^{-1}$ reference wavelength band was calculated as follows:

$$IAR_{\lambda,1} = \frac{\text{mean-centered integrated absorbance occurring in the 930-905 cm}^{-1}\text{ wavelength band}}{\text{mean-centered integrated absorbance occurring in the 890-880 cm}^{-1}\text{ reference wavelength band}}$$

Figure 5:
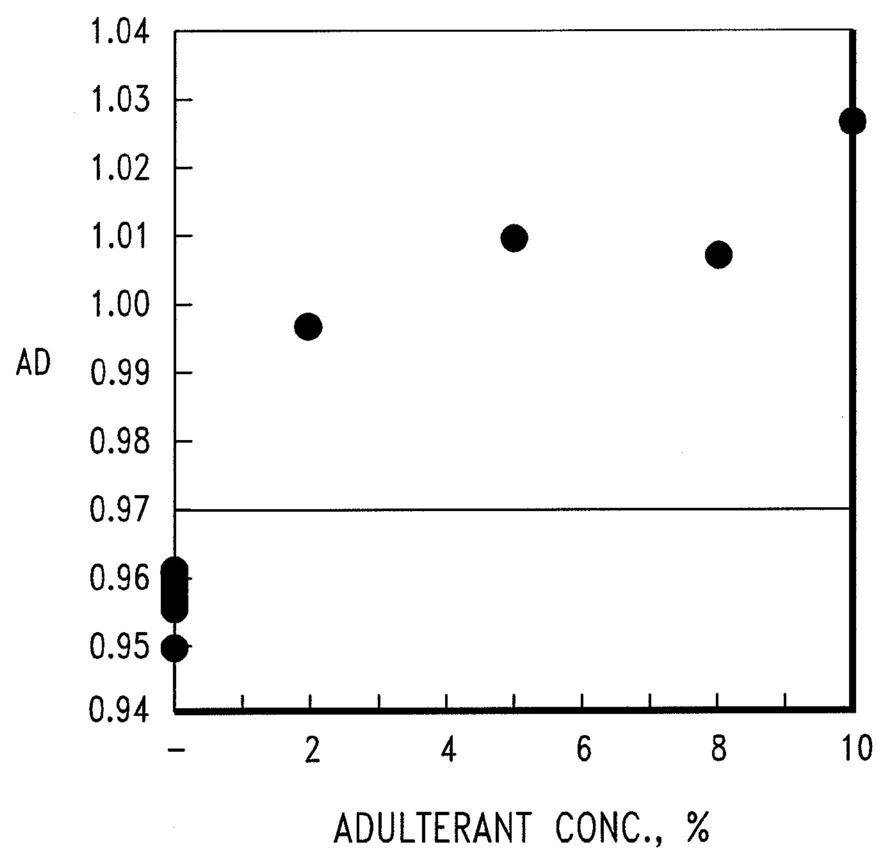
FIG. 5 is a graphical representation illustrating the relationship between the adulterant detection criterion (AD) and the adulterant concentration.

The above described mean-centered integrated absorbance ratio, i.e. $IAR_{\lambda,1}$, is used as an adulterant detection criterion (AD). In other words, $IAR_{\lambda,1}$=AD. Accordingly, a user of the food product, in this example olive oil, can establish a predetermined AD and then decide to accept or reject a food product depending upon the value of the measured AD. For example, FIG. 5 shows the measured AD for each of the previously mentioned adulterated olive oil samples, i.e. the olive oil samples containing 0%, 2%, 5%, 8%, and 10% sunflower oil. As shown in FIG. 5, each olive oil sample containing 0% sunflower oil has an AD<0.97. On the other hand, each olive oil sample containing 2% or greater sunflower oil has an AD>0.97. Therefore, a user of the olive oil could establish an AD of 0.97 for olive oil. Based upon an AD of 0.97 the user of the olive oil can decide to accept or reject a sample of olive oil. For example, based upon the data shown in FIG. 5 and an AD of 0.97, a user of olive oil would reject any sample having an AD greater than 0.97 as being adulterated, while accepting any sample having an AD less than 0.97 as being substantially pure.

However, note that a user of the olive oil could also set a different value for the AD depending upon the standards and ultimate use of the olive oil. For example, if the use of the olive oil does not require it to be substantially pure then a user could establish a 1.05 AD. In this case, all of the samples of olive oil shown in FIG. 5 would be accepted.

The following example illustrates utilizing one wavelength band for providing a measurement of milk fat in milk. However, it should be understood that the methods described herein can also be utilized to measure or detect the presence of other organic substances in milk or other food products. For example, the methods described herein can be utilized to detect the presence of cells or other contaminates in milk.

Figure 6:
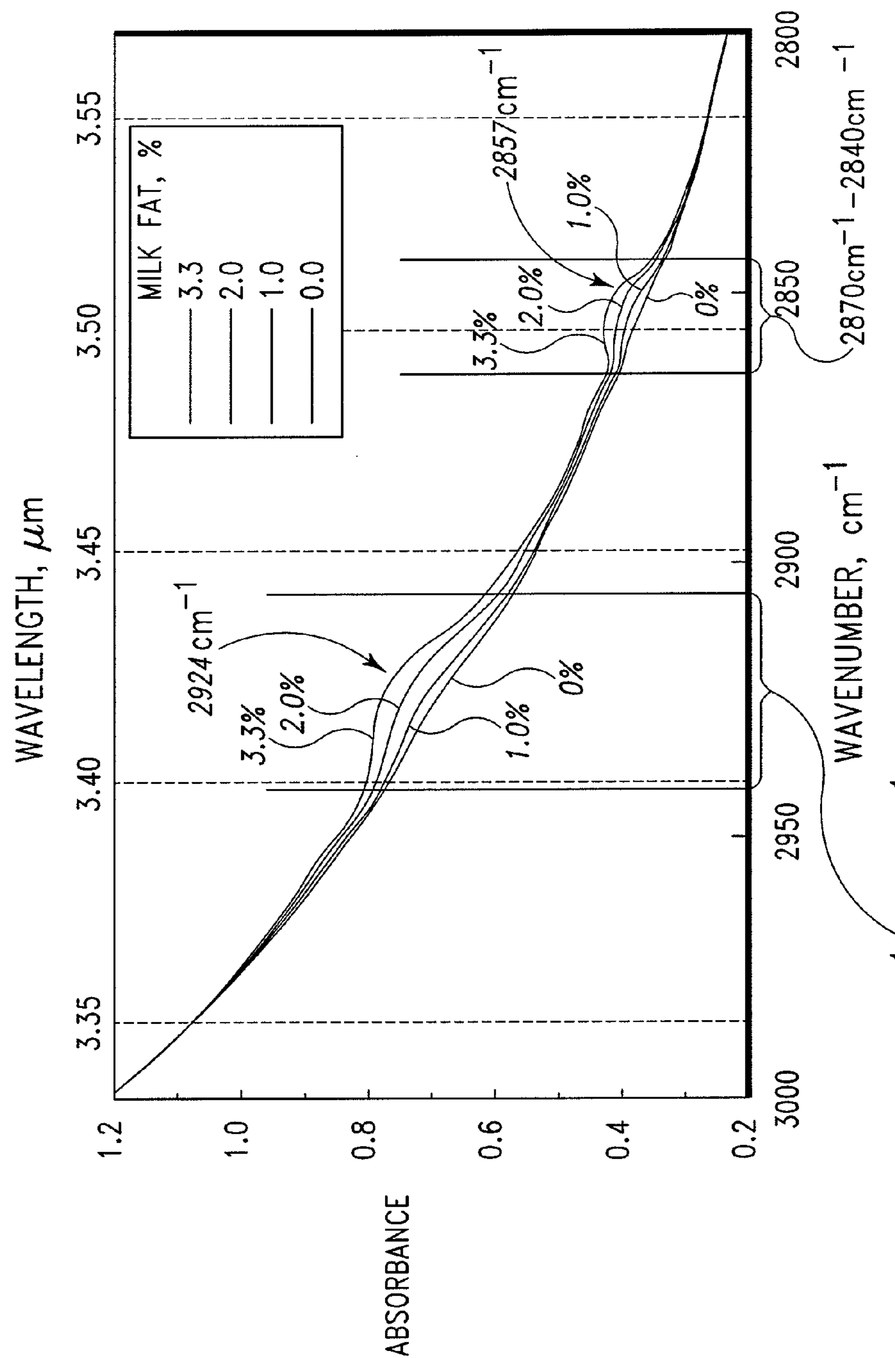
FIG. 6 is an ATR spectra of milk having different milk fat concentrations.
Figure 7A:
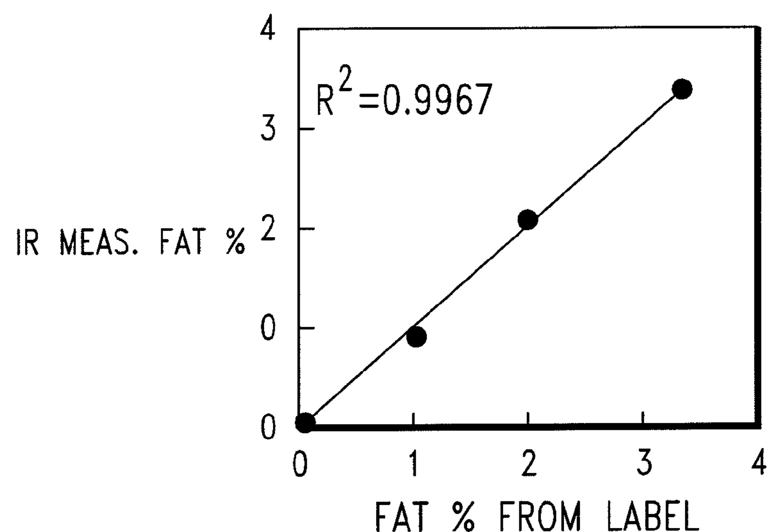
FIG. 7A is graph showing calibration results.
Figure 7B:
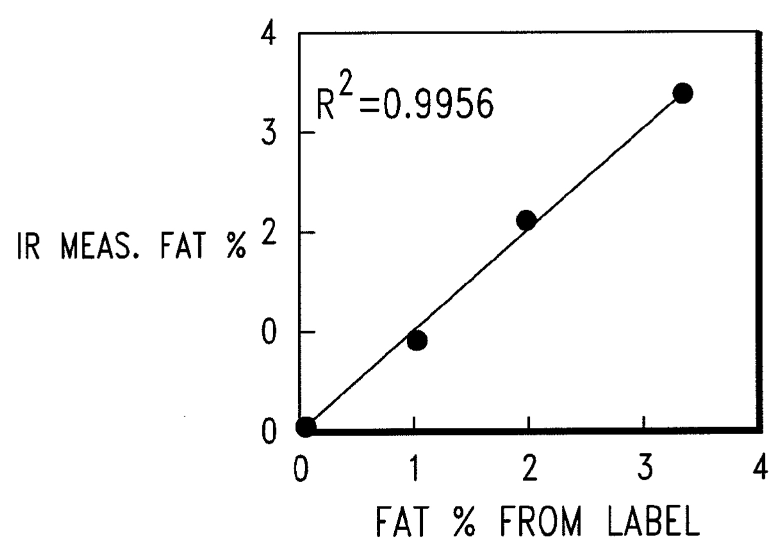
FIG. 7B is another graph showing calibration results.

As shown in FIG. 6, the absorption peaks due to the different components in milk are seen in the 3000-2800 $cm^{-1}$ (3.33-3.85 μm) range. In this figure, the major absorption peaks due to the $CH_2$ and $CH_3$ stretching are identifiable. Both absorption bands are suitable for the quantification of milk fat in milk. In particular, the absorption band occurring in the wavelength band of about 2905 $cm^{-1}$ to about 2945 $cm^{-1}$ (centered at about 2924 $cm^{-1}$) and the absorption band occurring in the wavelength band of about 2840 $cm^{-1}$ to about 2870 $cm^{-1}$ (centered at about 2857 $cm^{-1}$) are suitable for the quantification of milk fat in milk. The integrated absorbance occurring in one wavelength band (i.e. about 2905 $cm^{-1}$ to about 2945 $cm^{-1}$ or about 2840 $cm^{-1}$ to about 2870 $cm^{-1}$) is calculated from the measured spectra of milk having different concentrations of milk fat (i.e. 3.3%, 2.0%, 1.0%, 0.0%). The integrated absorbances are divided by the bandwidth to avoid scaling effects. The above values of milk fat concentrations (i.e. 3.3%, 2.0%, 1.0%, 0.0%) and the integrated absorbance were used to generate a regression model (using for example, Matlab 6.1.0.450 release 12.1) and to obtain calibration constants. The concentration of milk fat in milk was calibrated using the following equation:

$$C_f = P_0 + P_1 IA_{\lambda,1}$$

where (i) $C_f$ is the mean-centered known concentration of milk fat in the milk sample, (ii) $P_i$ are calibration constants, and (iii) $IA_{\lambda,1}$ is a mean-centered integrated absorbance occurring in the selected wavelength band. The results for quantifying milk fat in milk using the absorbance band centered at about 2924 cm−1 and the absorption band centered at about 2857 $cm^{-1}$ are shown in FIGS. 7A and 7B, respectively.

One configuration of a sensor (see FIGS. 2 and 3) based on this type of analysis may be reduced to just a single band measurement eliminating the direct signal measurement that is used to calculate the absorbance. The sensor will use the calibration constants and give the value of the milk fat concentration based on the signals from a single infrared filter-detection element or an IR LED and detector combination.

The following discussion is directed to obtaining useful measurements of the amount of vegetable oil contained within extra virgin olive oil. The samples were prepared as follows.

Materials and Methods

Samples

Thirty-two extra virgin olive oil and seven vegetable oil (Canola, walnut, sunflower, soybean, peanut, corn, sesame) samples were purchased from local grocery stores. The olive oil and sunflower samples were mixed to obtain the standard or trained sets of 32 pure and 17 adulterated samples. The amount of sunflower oil in olive oil ranged from 20 to 100 mL/L. The samples containing sunflower oils were marked as adulterated while olive oil samples were marked as pure olive oil and classified using the FTIR spectra. In the second part of the experiment, 32 olive oil samples and 7 vegetable oil samples were compared and classified.

Instrumentation and Spectral Acquisition

A ThermoNicolet Nexus 670 instrument equipped with a Mercury Cadmium Telluride A (MCTA) detector and KBr optics was used to measure the spectra of oil samples. The oil samples with different and known olive oil and sunflower oil composition were placed on a single bounce ZnSe ATR crystal. About 128 scans were taken and averaged and measurements were taken at a resolution of 2 $cm^{-1}$. The background was collected before every sample was measured.

Discriminant and Partial Least Squares (PLS) Analysis

Chemometric analysis including discriminant and PLS analysis were carried out using TQ analyst (ThermoNicolet) software package. The spectral regions where the variations were observed were chosen for developing the discriminant analysis and the PLS model. The first 12 factors were used for discriminant analysis model and the first 5 factors for the PLS model, which gave the 99.9% of spectral information.

Results and Discussion

Figure 8:
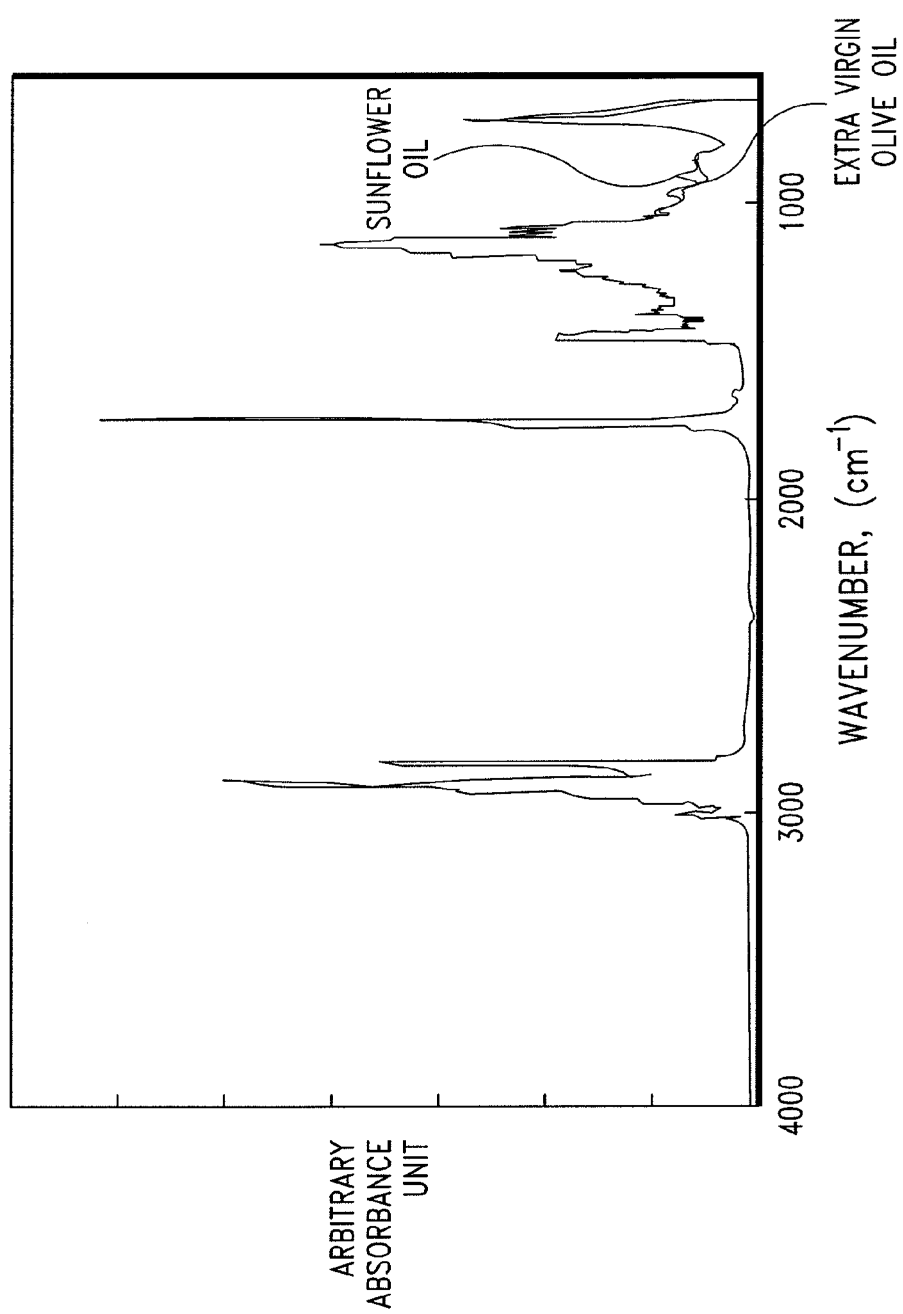
FIG. 8 is a spectra of extra virgin olive oil and sunflower oil.
Figure 9:
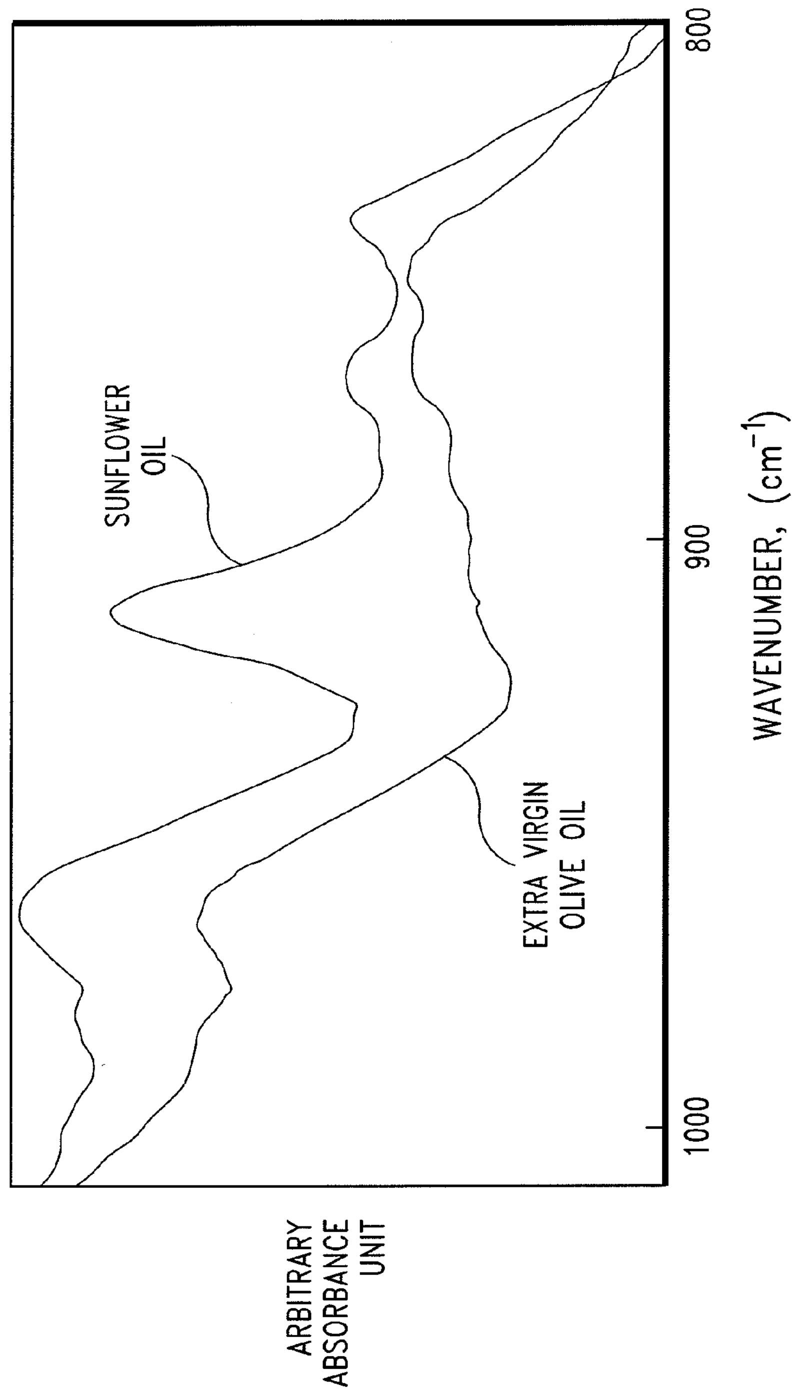
FIG. 9 is a finger print spectra of extra virgin olive oil and sunflower oil.

The typical spectra of extra virgin olive oil and sunflower oil are shown in FIG. 8. The prominent peaks due to C—H stretching mode in the wave number region of 2800-3100 $cm^{-1}$, C═O stretching in the region of 1700-1800 $cm^{-1}$ and C—O—C stretching and C—H bending in the region of 900-1400 $cm^{-1}$ can be easily observed. The entire range of spectra looks almost similar for both the oils unless one observes very closely. This is due to the similar chemical composition of the selected oils. Most of the spectral information used for the discriminant analysis is contained in the wave number regions of about 3100 $cm^{-1}$ to about 2800 $cm^{-1}$, and about 1800 $cm^{-1}$ to about 900 $cm^{-1}$. The major result of the method developed for the discriminant analysis relies on the exploitation of these small changes in the regions of interest. As discussed above, there are certain differences between the spectrum of extra virgin olive oil and sunflower oil in the fingerprint wave number region of about 800 $cm^{-1}$ to about 1200 $cm^{-1}$. These difference are shown again in FIG. 9.

Figure 10:
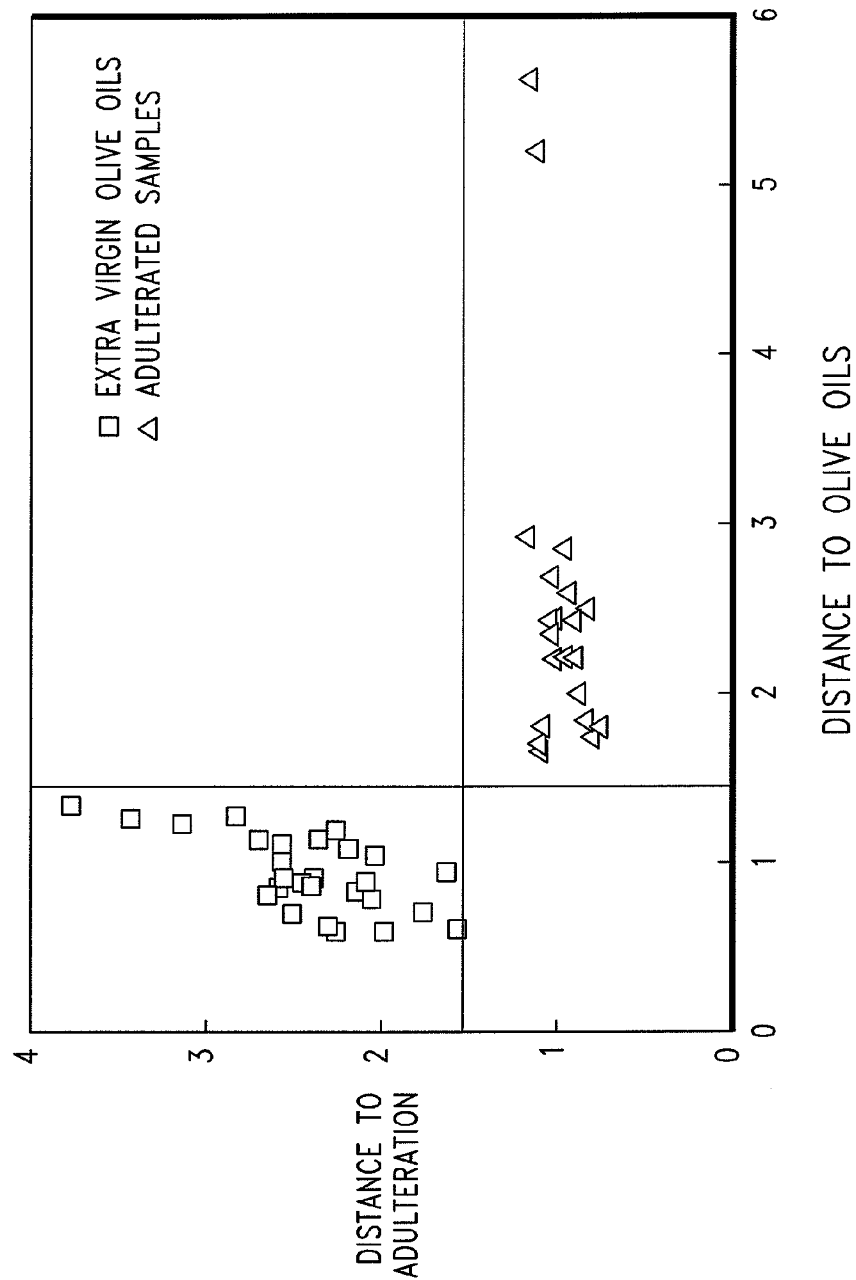
FIG. 10 is a Cooman plot for the classification of substantially pure extra virgin olive oil and adulterated olive oils.

The samples were classified into two groups: adulterated and pure extra virgin olive oils. Discriminant analysis was applied to both classes in the wave number regions of about 3100 $cm^{-1}$ to about 2800 $cm^{-1}$ and about 1800 $cm^{-1}$ to about 900 $cm^{-1}$. FIG. 10 shows a Cooman plot for the classification of pure extra virgin oils and adulterated olive oils with addition of 20-100 mL/L sunflower oil to extra virgin olive oils using 12 principal components for the classification. The x-axis shows the mahalanobis distance to the olive oil class while y-axis shows the distance to the adulterated oil class. The discriminant analysis model classified 100% of all samples accurately. The model was able to classify up to 20 mL/L adulteration level of sunflower oil. Table 1 (see below) shows the eigen analysis for 12 principal components (PC) and their analysis contribution.

TABLE 1

| Principle Component | Full Spectrum Contribution | Analysis Region Contribution |
|---|---|---|
| 1 | 61.8 | 91.2 |
| 2 | 79.1 | 95.4 |
| 3 | 87.3 | 97.6 |
| 4 | 91.7 | 98.3 |
| 5 | 95.0 | 98.7 |
| 6 | 96.8 | 99.1 |
| 7 | 97.5 | 99.3 |
| 8 | 98.0 | 99.5 |
| 9 | 98.4 | 99.7 |

It can be seen that with the first 6 principle components it is possible to extract about 99% of the desired information. This shows that there is sufficient variability in the method. Generally, for discriminant analysis the number of independent sources of spectral variation should be at least the same as the number of components or classes. The mahalanobis distance is a very useful way of determining the similarity or dissimilarity of a set of values from an unknown sample to a set of values measured from a collection of known samples. The mathematics of the mahalanobis distance calculation is well known and has been applied successfully for spectral discrimination in a number of cases. One of the main reasons the mahalanobis distance method was used in this study is that it is very sensitive to inter-variable changes in the training data. In addition, since the mahalanobis distance is measured in terms of standard deviations from the mean of the training samples, the reported matching values give a statistical measure of how well the spectrum of the unknown sample matches (or does not match) the original training spectra.

Figure 11:
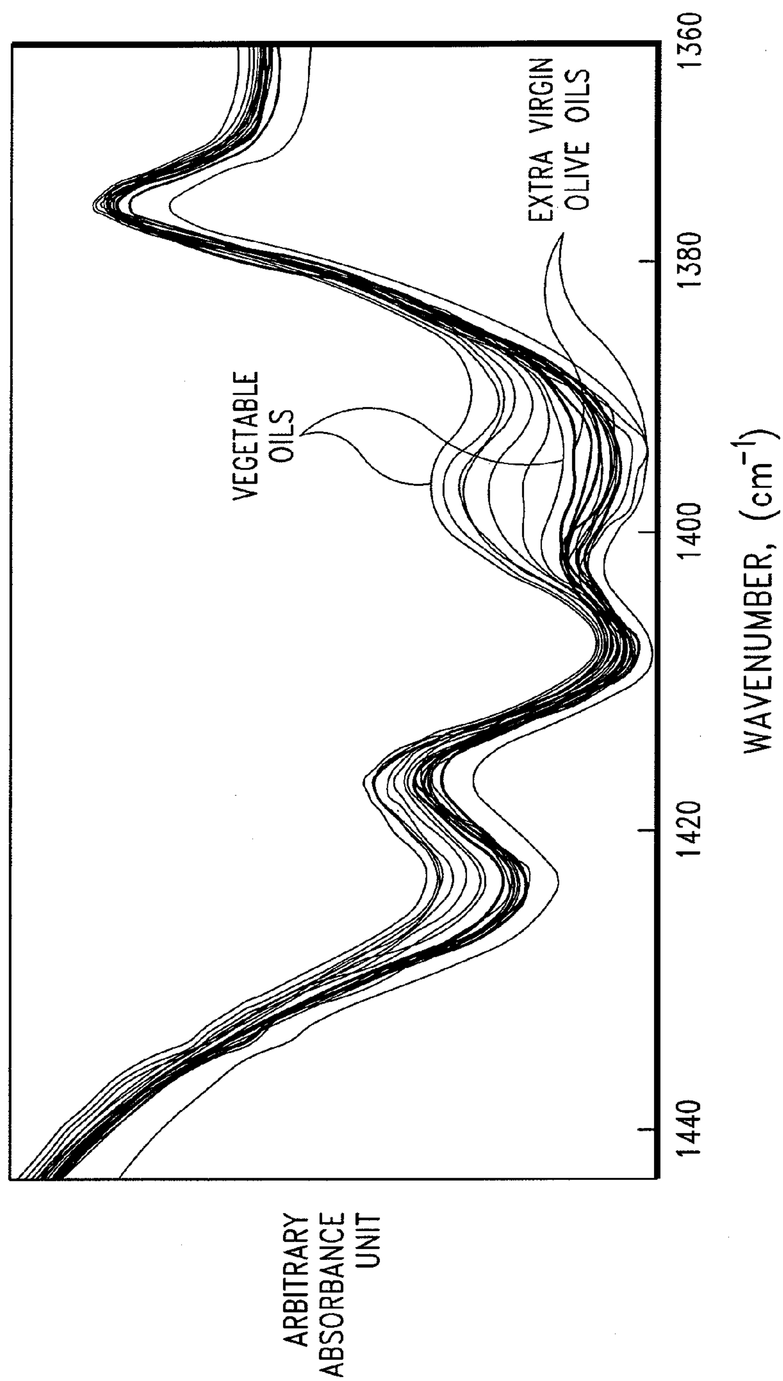
FIG. 11 is a plot showing the spectral variation between olive oil samples and vegetable seed oil samples in the finger print region.

In the second part of this study, the pure extra virgin olive oil samples were compared with the different vegetable oils such as soybean, peanut, walnut, sesame, canola, corn sunflower, and cottonseed oil. All vegetable oils were classified into one group and compared with the olive oil samples. Discriminant analysis was applied to classify the samples into extra virgin olive oil and vegetable oil. The spectral variation between olive oil samples and vegetable oil samples is shown in FIG. 11. There is a clear separation of curves for various oils near wave number 1400 $cm^{-1}$.

Figure 12:
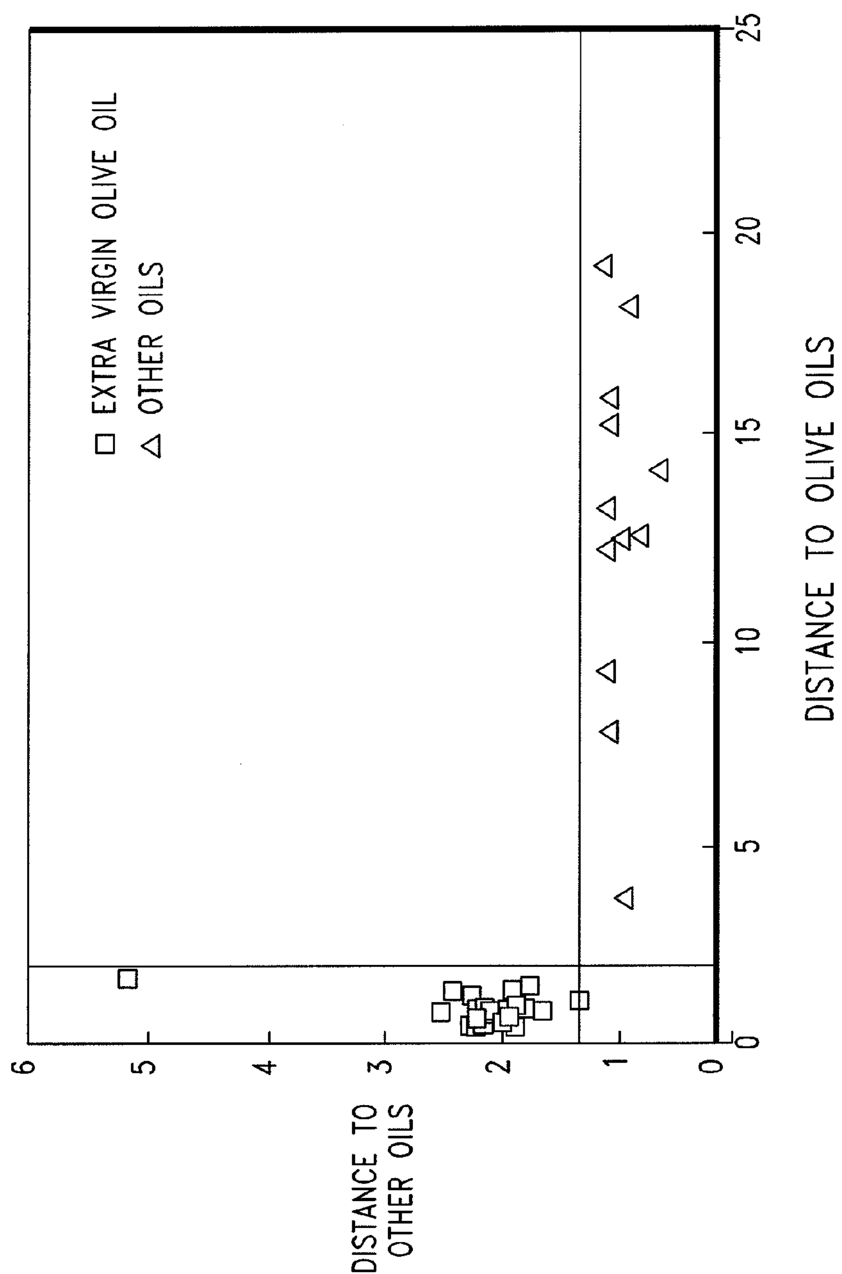
FIG. 12 is a Cooman plot of extra virgin olive oils and various vegetable seed oils.

FIG. 12 shows the Cooman plot of extra virgin olive oils and other vegetable oils. The model successfully classified olive oil samples and other vegetable oils. Table 2 (see below) shows the eigen analysis for 10 principal components and their analysis contribution for discriminant analysis.

TABLE 2

| Principle Component | Full Spectrum Contribution | Analysis Region Contribution |
|---|---|---|
| 1 | 64.7 | 97.6 |
| 2 | 96.7 | 99.1 |
| 3 | 98.6 | 99.6 |
| 4 | 99.1 | 99.7 |
| 5 | 99.4 | 99.8 |
| 6 | 99.5 | 99.9 |
| 7 | 99.7 | 99.9 |
| 8 | 99.7 | 99.9 |
| 9 | 99.8 | 99.9 |

It was possible to extract 97.6% of information from the first principle component. The mahalanobis distance from the Cooman plot revealed that walnut oil was the farthest and peanut oil was the closest vegetable oil to extra virgin olive oil samples.

Partial Least Squares (PLS) Analysis

Figure 13A:
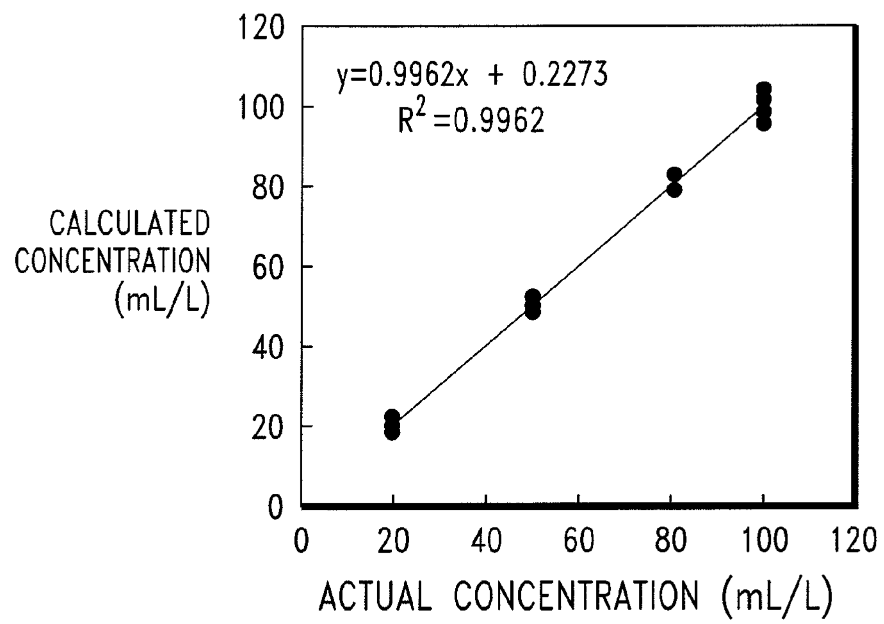
FIG. 13A is a graph showing concentration values for adulteration obtained from the PLS model versus actual concentration of sunflower oil.
Figure 13B:
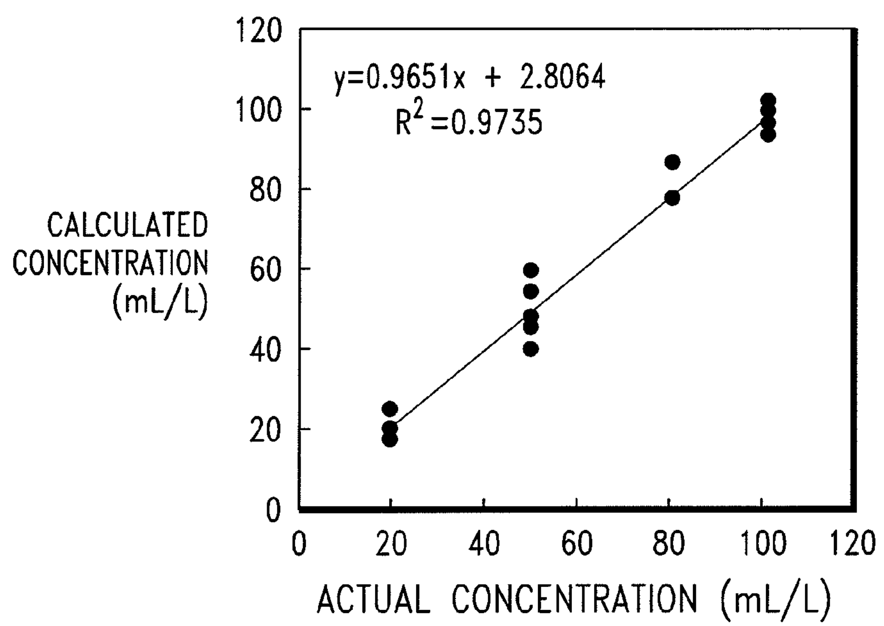
FIG. 13B is a plot showing cross validation of PLS by removing one standard at a time.
Figure 14:
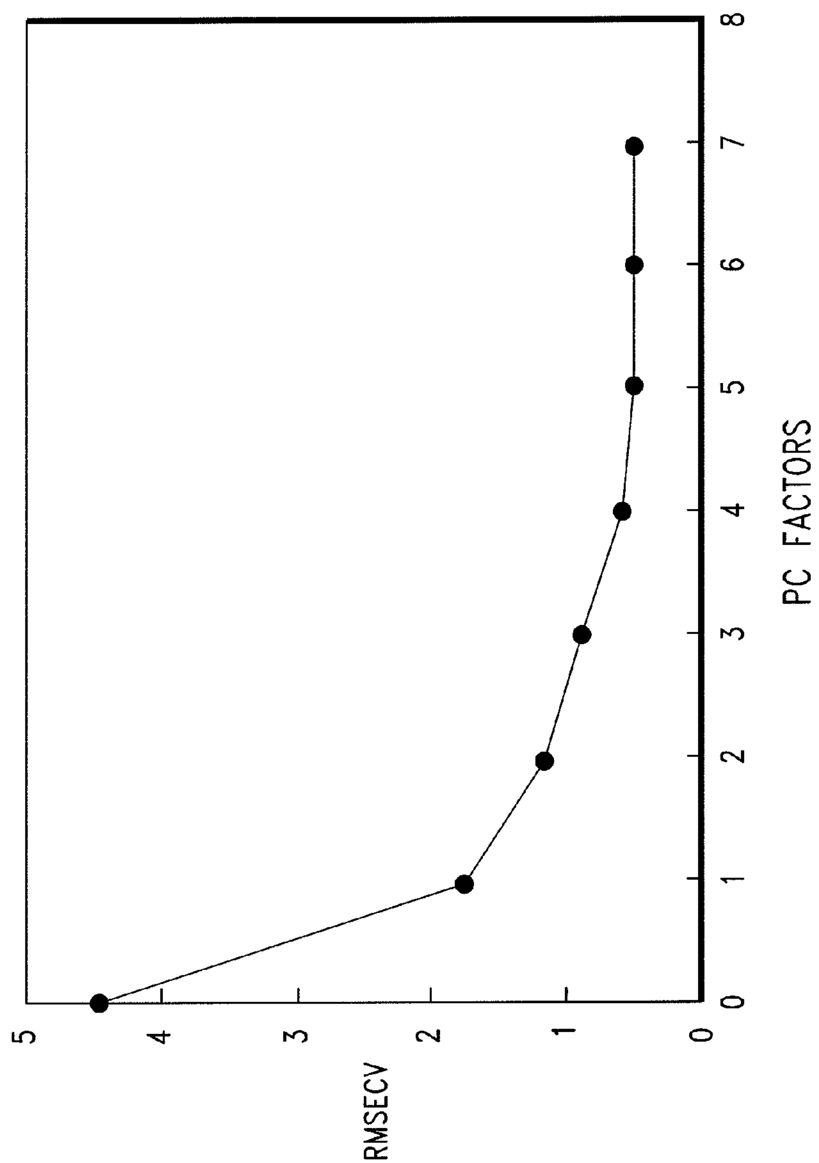
FIG. 14 is a plot showing the root mean square error of cross validation (RMSECV) versus PC factors.

In this part of the study, the results from discriminant analysis were confirmed using a PLS algorithm. Olive oil samples contaminated with 20 to 100 mL/L of sunflower oil were used for quantification purposes. The spectral region used for discriminant analysis was also used for PLS model. FIG. 13A shows the concentration values obtained from PLS model versus actual concentration of soybean oil in olive oil samples. The R-squared value for the PLS model was 0.996. The cross validation shows a reasonable R-squared value of 0.974. The cross validation was done by removing one standard at a time. The result from cross validation is shown in FIG. 13B. Confirmation and validation of the analysis region used for developing the PLS model were done by calculating the Predicted Residual Error Sum of Squares (PRESS) values for different PC factors. FIG. 14 shows that there is significant contribution from the first 2 PC factors. This confirms that the spectral region used for developing the PLS model for quantification of sunflower oil shows significant correlation with the concentration.

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected.

What is claimed is:

1. A method of measuring an amount of an organic substance contained within a food product, said organic substance having an infrared absorption spectrum which includes a set (n) of infrared absorption bands, the method comprising:

(a) passing infrared electromagnetic radiation through said food product containing said organic substance;

(b) detecting the intensity of infrared electromagnetic radiation passing through said food product containing said organic substance in ranges of wavelengths corresponding to each of a subset of said (n) infrared absorption bands to provide electrical signals corresponding thereto;

(c) processing said electrical signals with a quantification algorithm so as to provide a measurement of said amount of said organic substance contained within said food product, wherein said quantification algorithm includes dividing a first wavelength band integrated absorbance value by a reference wavelength band integrated absorbance value in which said organic substance does not substantially absorb said infrared electromagnetic radiation; and (d) outputting said measurement.

2. The method of claim 1, wherein:

(b) includes detecting the intensity of (i) about a 905-930 $cm^{-1}$ wavelength band of infrared electromagnetic radiation and (ii) about a 880-890 $cm^{-1}$ reference wavelength band of infrared electromagnetic radiation in which said organic substance does not substantially absorb said infrared electromagnetic radiation, and said quantification algorithm of (c) includes dividing said 905-930 $cm^{-1}$ wavelength band integrated absorbance value by said 880-890 $cm^{-1}$ reference wavelength band integrated absorbance value.

3. The method of claim 1, wherein:

(b) includes detecting the intensity of (i) about a 2905-2945 $cm^{-1}$ wavelength band of infrared electromagnetic radiation and/or (ii) about a 2840-2870 $cm^{-1}$ wavelength band of infrared electromagnetic radiation.

4. The method of claim 1, wherein:

said subset of said (n) wavelength bands of (b) is within a range defined by 800-1000 $cm^{-1}$.

5. The method of claim 1, wherein:

said subset of said (n) wavelength bands of (b) is within a range defined by 2800-3000$cm^{-1}$.

6. A method of measuring an amount of a vegetable seed oil in a food product, wherein said vegetable seed oil has an infrared absorption spectrum which includes a set (n) of infrared absorption bands, the method comprising:

(a) passing infrared electromagnetic radiation through said food product containing said vegetable seed oil;

(b) detecting the intensity of infrared electromagnetic radiation passing through said food product containing said vegetable seed oil in ranges of wavelengths corresponding to each of a subset of said (n) infrared absorption bands to provide electrical signals corresponding thereto;

(c) processing said electrical signals with a quantification algorithm so as to provide a measurement of said amount of said vegetable seed oil contained within said food product, wherein said vegetable seed oil does not substantially absorb said infrared electromagnetic radiation in a reference wavelength band, and said quantification algorithm includes dividing a first wavelength band integrated absorbance value by a reference wavelength band integrated absorbance value; and (d) outputting said measurement.

7. The method of claim 6, wherein:

(b) includes detecting the intensity of (i) about a 905-930 $cm^{-1}$ wavelength band of infrared electromagnetic radiation and (ii) about a 880-890 $cm^{-1}$ reference wavelength band of infrared electromagnetic radiation.

8. The method of claim 6, wherein:

said subset of said (n) wavelength bands of (b) is within a range defined by 800-1000 $cm^{-1}$.

9. The method of claim 6, wherein:

said food product includes olive oil.

10. A method of measuring an amount of milk fat in a food product, wherein said milk fat has an infrared absorption spectrum which includes a set (n) of infrared absorption bands, the method comprising:

(a) passing infrared electromagnetic radiation through said food product containing said milk fat;

(b) detecting the intensity of infrared electromagnetic radiation passing through said food product containing said milk fat in ranges of wavelengths corresponding to each of a subset of said (n) infrared absorption bands to provide electrical signals corresponding thereto;

(c) processing said electrical signals with a quantification algorithm so as to provide a measurement of said amount of said milk fat contained within said food product, wherein said quantification algorithm includes dividing a first wavelength band integrated absorbance value by a reference wavelength band integrated absorbance value in which said milk fat does not substantially absorb said infrared electromagnetic radiation; and (d) outputting said measurement.

11. The method of claim 10, wherein:

(b) includes detecting the intensity of about a 2905-2945 $cm^{-1}$ wavelength band of infrared electromagnetic radiation.

12. The method of claim 10, wherein:

(b) includes detecting the intensity of about a 2840-2870 $cm^{-1}$ wavelength band of infrared electromagnetic radiation.

13. The method of claim 10, wherein:

said subset of said (n) wavelength bands of (b) is within a range defined by 2800-3000 $cm^{-1}$.

14. The method of claim 10, wherein:

said food product includes milk.

15. A method of measuring a concentration of an organic substance contained within a food product, said organic substance having an infrared absorption spectrum which includes a set (n) of infrared absorption bands and one or more reference wavelengths bands, wherein said organic substance does not substantially absorb said infrared electromagnetic radiation in said one or more reference wavelength bands, the method comprising:

(a) detecting the intensity of infrared electromagnetic radiation influenced by said organic substance in ranges of wavelengths corresponding to each of a subset of said (n) infrared absorption bands and in ranges of wavelengths corresponding to each of a subset of said one or more reference wavelength bands to provide electrical signals corresponding thereto;

(b) processing said electrical signals with a mathematical model so as to provide a measurement of the concentration of said organic substance contained within said food product; and (c) outputting said measurement.

16. The method of claim 15, wherein:

(a) includes detecting the intensity of said infrared electromagnetic radiation influenced by a vegetable seed oil contained within said food product.

17. The method of claim 15, wherein:

(a) includes detecting the intensity of said infrared electromagnetic radiation influenced by milk fat contained within said food product.

18. The method of claim 15, wherein:

said mathematical model of (b) includes dividing an integrated absorbance value of one of said subset of said absorption bands by an integrated absorbance value of one of said subset of said reference wavelength bands.

19. The method of claim 15, wherein:

said mathematical model of (b) includes the mathematical equation $$C_f = P_0 + P_1 IA_{\lambda,1}$$

where (i) $C_f$ is a mean-centered known concentration of milk fat in a food product, (ii) $P_i$ are calibration constants, and (iii) $IA_{\lambda,1}$ is a mean-centered integrated absorbance occurring in a selected wavelength band.

20. A method of measuring an amount of an organic substance contained within a food product, said organic substance having an infrared absorption spectrum which includes a set (n) of infrared absorption bands, the method comprising:

(a) passing infrared electromagnetic radiation through said food product containing said organic substance;

(b) passing infrared electromagnetic radiation passing through said food product containing said organic substance through a filter so that only electromagnetic radiation in ranges of wavelengths corresponding to a subset of said (n) infrared absorption bands is allowed to pass to a detector;

(c) detecting the intensity of infrared electromagnetic radiation passing through said filter to provide electrical signals corresponding thereto;

(d) processing said electrical signals with a quantification algorithm so as to provide a measurement of said amount of said organic substance contained within said food product; and (e) outputting said measurement.

21. A method of measuring an amount of an organic substance contained within a food product, said organic substance having an infrared absorption spectrum which includes a set (n) of wavelength regions, wherein each of said wavelength regions substantially correspond to an absorption band of said absorption spectrum, comprising:

(a) illuminating said food product with infrared electromagnetic radiation;

(b) detecting the intensity of said infrared electromagnetic radiation that is absorbed by said organic substance contained within said food product, wherein (i) said intensity detection is restricted to a number of selected wavelength bands of infrared electromagnetic radiation, (ii) each of said selected wavelength bands substantially corresponds to one of said wavelength regions, and (iii) said number of said selected wavelength bands is a subset of (n);

(c) generating an electrical signal in response to detecting the intensity of said subset of said selected wavelength bands;

(d) receiving said electrical signal with a signal processor configured to process said electrical signal with a quantification algorithm; and (e) processing said electrical signal with said quantification algorithm so as to provide a measurement of said amount of said organic substance contained within said food product; and (f) outputting said measurement, wherein (b) includes detecting the intensity of one or more reference wavelengths bands of said infrared electromagnetic radiation which are not substantially absorbed by said organic substance contained within said food product, and wherein (c) includes generating said electrical signal in response to detecting the intensity of said one or more reference wavelength bands.

22. A method of measuring an amount of an organic substance contained within a food product, said organic substance having an infrared absorption spectrum which includes a set (n) of infrared absorption bands and one or more reference wavelengths bands, wherein said organic substance does not substantially absorb said infrared electromagnetic radiation in said one or more reference wavelength bands, the method comprising:

(a) illuminating said food product with infrared electromagnetic radiation from an IR source;

(b) detecting the intensity of said infrared electromagnetic radiation influenced by said organic substance in a range of wavelengths corresponding to one of said absorption bands and a range of wavelengths corresponding to one of said reference wavelength bands to provide electrical signals corresponding thereto;

(c) processing said electrical signals with a mathematical model to provide a measurement of said amount of said organic substance contained within said food product; and (d) outputting said measurement.

23. The method of claim 22, wherein said quantification algorithm includes dividing an integrated absorbance value of said one of said absorption bands by an integrated absorbance value of said one of said reference wavelength bands.

24. An apparatus for measuring an amount of an organic substance contained within a food product, said organic substance having an infrared absorption spectrum which includes a set (n) of infrared absorption bands and one or more reference wavelengths bands, wherein said organic substance does not substantially absorb said infrared electromagnetic radiation in said one or more reference wavelength bands, the apparatus comprising (a) a detector operable to detect the intensity of infrared electromagnetic radiation passing through said food product containing said organic substance in a range of wavelengths corresponding to one of said infrared absorption bands and a range of wavelengths corresponding to one of said reference wavelength bands to provide electrical signals corresponding thereto; and (b) a processor operable to process said electrical signals with a quantification algorithm so as to provide a measurement of said amount of said organic substance contained within said food product.

25. An apparatus for measuring an amount of an organic substance contained within a food product, said organic substance having an infrared absorption spectrum which includes a set (n) of infrared absorption bands and one or more reference wavelengths bands, wherein said organic substance does not substantially absorb said infrared electromagnetic radiation in said one or more reference wavelength bands, the apparatus comprising (a) a detector operable to detect the intensity of infrared electromagnetic radiation influenced by said organic substance in a range of wavelengths corresponding to one of said infrared absorption bands and a range of wavelengths corresponding to one of said reference wavelength bands to provide electrical signals corresponding thereto; and (b) a processor operable to process said electrical signals with a quantification algorithm so as to provide a measurement of said amount of said organic substance contained within said food product.

* * * * *